US010215725B2

(12) United States Patent
Sekiya et al.

(10) Patent No.: US 10,215,725 B2
(45) Date of Patent: Feb. 26, 2019

(54) SENSOR ELEMENT AND GAS SENSOR

(71) Applicant: NGK Insulators, Ltd., Nagoya (JP)

(72) Inventors: Takayuki Sekiya, Nisshin (JP); Mika Murakami, Nagoya (JP); Naoya Saito, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 14/672,793

(22) Filed: Mar. 30, 2015

(65) Prior Publication Data

US 2015/0276657 A1     Oct. 1, 2015

(30) Foreign Application Priority Data

Mar. 31, 2014  (JP) ................................. 2014-072927
Mar. 26, 2015  (JP) ................................. 2015-063961

(51) Int. Cl.
*G01N 27/407*        (2006.01)
(52) U.S. Cl.
CPC ............................... *G01N 27/4072* (2013.01)
(58) Field of Classification Search
CPC ..................................... G01N 27/404–27/4074
See application file for complete search history.

(56) References Cited

U.S. PATENT DOCUMENTS

| 5,419,828 A * | 5/1995 | Nakano | G01N 27/4073 |
| | | | 204/425 |
| 6,036,841 A | 3/2000 | Kato et al. | |
| 6,071,393 A * | 6/2000 | Oshima | G01N 27/4074 |
| | | | 204/425 |
| 2003/0106795 A1 | 6/2003 | Katafuchi et al. | |
| 2004/0069629 A1 | 4/2004 | Tanaka et al. | |
| 2004/0188251 A1 | 9/2004 | Kurachi et al. | |
| 2009/0229978 A1 | 9/2009 | Mizutani et al. | |

(Continued)

FOREIGN PATENT DOCUMENTS

DE  10 2009 020 841 A1   12/2009
DE  10 2008 040 175 A1    1/2010

(Continued)

OTHER PUBLICATIONS

Extended European Search Report (Application No. 15161770.1) dated Aug. 3, 2015.

(Continued)

*Primary Examiner* — J. Christopher Ball
(74) *Attorney, Agent, or Firm* — Burr & Brown, PLLC

(57) ABSTRACT

In a sensor element, a fourth diffusion rate-controlling portion includes a diffusion rate-controlling portion. The diffusion rate-controlling portion is formed between one or more and three or less surfaces, e.g., an upper surface, of upper, lower, left and right inner peripheral surfaces of a measurement-object gas flowing portion and a partition wall. A measurement electrode is formed on one, e.g., a lower surface, of upper, lower, left and right inner peripheral surfaces of a third inner cavity, the one surface being different in orientation from the Csurface along which the diffusion rate-controlling portion is formed. The diffusion rate-controlling portion and the measurement electrode may be formed on surfaces opposite to each other. A distance L between the measurement electrode and the diffusion rate-controlling portion may be 0.1 mm or more.

10 Claims, 9 Drawing Sheets

(56) References Cited

U.S. PATENT DOCUMENTS

| | | | |
|---|---|---|---|
| 2009/0242404 A1* | 10/2009 | Miyashita | G01N 27/4071 204/431 |
| 2009/0280240 A1 | 11/2009 | Ohya et al. | |
| 2011/0083490 A1 | 4/2011 | Murakami et al. | |
| 2011/0147214 A1 | 6/2011 | Fujita et al. | |

FOREIGN PATENT DOCUMENTS

| | | |
|---|---|---|
| EP | 0 791 828 A1 | 8/1997 |
| EP | 0 869 356 A2 | 10/1998 |
| EP | 0 971 228 A2 | 1/2000 |
| EP | 1 464 954 A2 | 10/2004 |
| EP | 1 731 903 A1 | 12/2006 |
| JP | H09-288087 A1 | 11/1997 |
| JP | 10-325825 A | 12/1998 |
| JP | 2004-093200 A1 | 3/2004 |
| JP | 2004-317496 A | 11/2004 |
| JP | 2009-222561 A1 | 10/2009 |
| JP | 2011-102793 A | 5/2011 |
| JP | 2011-102797 A | 5/2011 |
| JP | 4911910 B | 4/2012 |
| JP | 2013-140175 A1 | 7/2013 |

OTHER PUBLICATIONS

Third Party Submission, Japanese Application No. 2015-063961, dated Jan. 30, 2018 (5 pages).
European Office Action, European Application No. 15161770.1, dated Jun. 28, 2017 (8 pages).
Japanese Office Action (Application No. 2015-063961) dated Aug. 28, 2018 (with English translation).

* cited by examiner

SENSOR ELEMENT AND GAS SENSOR

BACKGROUND OF THE INVENTION

1. Field of the Invention

The present invention relates to a sensor element and a gas sensor.

2. Description of the Related Art

There is so far known a gas sensor for detecting the concentration of a specific gas, e.g., NOx, in measurement object gas to be measured, such as automobile exhaust gas. For example, Patent Literatures (PTL) 1 and 2 disclose a gas sensor including a sensor element that has an elongate plate-like shape, and that is formed by stacking a plurality of gas-tight oxygen ion-conductive solid electrolyte layers.

FIG. 15 is a schematic sectional view illustrating, in a simplified fashion, one example of a structure of a gas sensor 300 of the above-mentioned related art. As illustrated in FIG. 15, the gas sensor 300 includes a sensor element 307. The sensor element 307 is an element of a multilayer structure in which dense oxygen ion-conductive solid electrolyte layers 301 to 306 are stacked. In the sensor element 307, a measurement-object gas flowing portion through which measurement object gas is introduced is formed between a lower surface of the solid electrolyte layer 306 and an upper layer of the solid electrolyte layer 304. The measurement-object gas flowing portion includes a gas introducing region 310, and first to third inner cavities 320, 340 and 361. An inner pump electrode 322 is formed in the first inner cavity 320, an auxiliary pump electrode 351 is formed in the second inner cavity 340, and a measurement electrode 344 is formed on a lower surface of the third inner cavity 361 (i.e., an upper surface of the solid electrolyte layer 304). Furthermore, an outer pump electrode 323 is formed on an upper surface of the solid electrolyte layer 306. In the gas sensor 300, when the measurement object gas is introduced to the first inner cavity 320 in the measurement-object gas flowing portion, oxygen is pumped out or pumped in between the first inner cavity 320 and the outside of the sensor element 307 in accordance with a control voltage Vp0 that is applied between the outer pump electrode 323 and the inner pump electrode 322. Subsequently, when the measurement object gas is introduced to the second inner cavity 340, oxygen is pumped out or pumped in between the second inner cavity 340 and the outside of the sensor element 307 in accordance with a control voltage Vp1 that is applied between the outer pump electrode 323 and the auxiliary pump electrode 351. After the oxygen concentration of the measurement object gas has been controlled as described above during passage of the measurement object gas through the first inner cavity 320 and the second inner cavity 340, the measurement object gas is introduced to the third inner cavity 361. The concentration of a specific gas in the measurement object gas is then detected on the basis of a current Ip2 that flows when oxygen is pumped out or pumped in through the outer pump electrode 323 and the measurement electrode 344.

Moreover, the third inner cavity 361 is partitioned from the second inner cavity 340 by a partition wall 356. Diffusion rate-controlling portions 354 each having a slit-like shape are formed between the partition wall 356 and an upper surface of the measurement-object gas flowing portion (i.e., the lower surface of the solid electrolyte layer 306) and between the partition wall 356 and a lower surface of the measurement-object gas flowing portion (i.e., the upper surface of the solid electrolyte layer 304). The diffusion rate-controlling portions 354 give predetermined diffusion resistance to the measurement object gas that is introduced to the second inner cavity 340. Thus, an abrupt change in concentration of the measurement object gas reaching the measurement electrode 344 in the second inner cavity 340 is suppressed.

CITATION LIST

Patent Literature

PTL 1: JP 2011-102797 A
PTL 2: JP 2011-102793 a

SUMMARY OF THE INVENTION

In the related-art gas sensor of the above-described type, the measurement electrode may deteriorate with the continued use of the gas sensor, and sensitivity in detecting the concentration of the specific gas may reduce in some cases. In the gas sensor 300 of FIG. 15, for example, the current Ip2 may reduce even at the same concentration of the specific gas in some cases.

The present invention has been made in view of the above-mentioned problem, and a main object of the present invention is to suppress reduction in sensitivity of a measurement electrode in a sensor element.

To achieve the above object, the present invention is constituted with the following means.

The sensor element according to a first aspect of the present invention comprises a layered body that is formed by stacking a plurality of oxygen ion-conductive solid electrolyte layers, and that includes a measurement-object gas flowing portion formed therein to introduce measurement object gas from outside, a measurement electrode mounting space that is a part of the measurement-object gas flowing portion, and that is partitioned from an inflow side of the measurement object gas by a partition wall, at least one diffusion rate-controlling portion that is a part of the measurement-object gas flowing portion, that is formed, assuming a direction in which the solid electrolyte layers are stacked to be an up and down direction and a direction perpendicular to both the up and down direction and a direction in which the measurement object gas flows to be a right and left direction, between one or more and three or less surfaces of upper, lower, left and right inner peripheral surfaces of the measurement-object gas flowing portion and the partition wall, and that serves as a flow path through which the measurement object gas is introduced to the measurement electrode mounting space, and a measurement electrode that is formed on one of upper, lower, left and right inner peripheral surfaces of the measurement electrode mounting space, the one surface being different in orientation from the at least one surface along which the diffusion rate-controlling portion is formed.

In the sensor element according to the first aspect of the present invention, the measurement electrode mounting space partitioned from the inflow side of the measurement object gas by the partition wall is formed in a part of the measurement-object gas flowing portion. At least one diffusion rate-controlling portion serving as the flow path through which the measurement object gas is introduced to the measurement electrode mounting space is formed between the inner peripheral surface of the measurement-object gas flowing portion and the partition wall. The measurement electrode is formed on the inner peripheral surface of the measurement electrode mounting space. More specifically, the diffusion rate-controlling portion is formed between one or more and three or less surfaces of the upper, lower, left and right inner peripheral surfaces of the measurement-object gas flowing portion and the partition wall. The measurement electrode is formed on one of the upper, lower, left and right inner peripheral surfaces of the measurement electrode mounting space, the one surface being different in orientation from the surface along which the diffusion rate-controlling portion is formed. With such an arrangement, reduction of sensitivity of the measurement electrode can be suppressed. The reason is presumably as follows. When the measurement electrode is formed on a surface that is positioned in the same orientation as the surface, along which the diffusion rate-controlling portion is formed (e.g., the lower surface of the measurement-object gas flowing portion in FIG. 15), in any of the up and down direction and the right and left direction, the measurement object gas tends to move toward the measurement electrode along the surface along which the diffusion rate-controlling portion is formed. Therefore, a portion of the measurement electrode, which is positioned nearer to its end on the same side as the diffusion rate-controlling portion, tends to be exposed to the measurement object gas having higher concentration with higher possibility. As a result, an end of the measurement electrode and its portion near that end on the same side as the diffusion rate-controlling portion mainly fulfill the function as the measurement electrode, and deterioration of the measurement electrode progresses in such an end region in a concentrated fashion. Accordingly, the sensitivity of the measurement electrode is more apt to reduce. In contrast, in the sensor element according to the first aspect of the present invention, the measurement electrode is formed on one of the upper, lower, left and right inner peripheral surfaces of the measurement electrode mounting space, the one surface being different in orientation from the surface along which the diffusion rate-controlling portion is formed. With such an arrangement, the measurement object gas having passed through the diffusion rate-controlling portion reaches the measurement electrode after having diffused in the measurement electrode mounting space. Accordingly, the concentration of the measurement object gas contacting the measurement electrode is less likely to become uneven, for example, between the side closer to the diffusion rate-controlling portion and the side opposite to the former. As a result, the measurement electrode can more reliably fulfill the function as a measurement electrode in its entirety, and deterioration of the measurement electrode progresses moderately as a whole. Comparing with the case where the measurement electrode is formed on the surface positioned in the same orientation as the surface along which the diffusion rate-controlling portion is formed, therefore, the reduction in sensitivity of the measurement electrode can be further suppressed.

In the sensor element according to the first aspect of the present invention, the diffusion rate-controlling portion may be formed between one of the upper, lower, left and right inner peripheral surfaces of the measurement-object gas flowing portion and the partition wall, and the measurement electrode may be formed on one of the upper, lower, left and right inner peripheral surfaces of the measurement electrode mounting space, the one surface being positioned on the side opposite to the surface along which the diffusion rate-controlling portion is formed. With such an arrangement, the diffusion rate-controlling portion and the measurement electrode are positioned farther away from each other in comparison with the case where the measurement electrode is formed on the surface that is different in orientation from the surface along which the diffusion rate-controlling portion is formed, but that is not positioned on the side opposite to the latter surface. Accordingly, the measurement object gas is more apt to diffuse in the measurement electrode mounting space before the measurement object gas having passed through the diffusion rate-controlling portion reaches the measurement electrode. As a result, the above-described effect of suppressing the reduction in sensitivity of the measurement electrode is further increased. In this respect, the diffusion rate-controlling portion may be formed between one of the upper and lower inner peripheral surfaces of the measurement-object gas flowing portion and the partition wall, and the measurement electrode may be is formed on one of the upper and lower inner peripheral surfaces of the measurement electrode mounting space, the one surface being positioned on the side opposite to the surface along which the diffusion rate-controlling portion is formed. With such an arrangement, the diffusion rate-controlling portion and the measurement electrode can be formed more easily than in the case where the diffusion rate-controlling portion and the measurement electrode are formed along and on the right and left inner peripheral surfaces in opposite relation.

In the sensor element according to the first aspect of the present invention, a distance L between the measurement electrode and the diffusion rate-controlling portion may be 0.1 mm or more. In such a case, the diffusion rate-controlling portion and the measurement electrode are positioned farther away from each other. Therefore, the measurement object gas is more apt to diffuse in the measurement electrode mounting space before the measurement object gas having passed through the diffusion rate-controlling portion reaches the measurement electrode. As a result, the above-described effect of suppressing the reduction in sensitivity of the measurement electrode is further increased.

A sensor element according to a second aspect of the present invention comprises a layered body that is formed by stacking a plurality of oxygen ion-conductive solid electrolyte layers, and that includes a measurement-object gas flowing portion formed therein to introduce measurement object gas from outside, a measurement electrode mounting space that is a part of the measurement-object gas flowing portion, at least one diffusion rate-controlling portion that is a part of the measurement-object gas flowing portion, and that serves as a flow path through which the measurement object gas is introduced to the measurement electrode mounting space from the outside, and a measurement electrode that is formed in the measurement electrode mounting space at a position where a distance L between the measurement electrode and the diffusion rate-controlling portion is 0.1 mm or more.

In the sensor element according to the second aspect of the present invention, the distance L between the measurement electrode and the diffusion rate-controlling portion is 0.1 mm or more, and the diffusion rate-controlling portion and the measurement electrode are positioned relatively away from each other. As in the sensor element according to the first aspect of the present invention, therefore, the measurement object gas is more apt to diffuse in the measurement electrode mounting space before the measurement object gas having passed through the diffusion rate-controlling portion reaches the measurement electrode. As a result, the reduction in sensitivity of the measurement electrode can be further suppressed in comparison with the case where the distance L is less than 0.1 mm.

In the sensor element according to the second aspect of the present invention, the measurement electrode may be formed on one of inner peripheral surfaces of the measurement electrode mounting space, the one surface being oriented perpendicularly to a flowing direction of the measurement object gas and positioned on the downstream side in the flowing direction.

The gas sensor of the present invention includes the sensor element according to the first aspect of the present invention or the sensor element according to the second aspect of the present invention, the sensor element having any of the above-described forms. Therefore, the gas sensor of the present invention can provide similar advantageous effects to those obtained with the sensor elements according to the first and second aspects of the present invention, e.g., the effect of suppressing the reduction of sensitivity of the measurement electrode.

In the gas sensor of the present invention, the layered body may have a reference gas introducing space formed therein to introduce reference gas therethrough, which is used as a reference to detect concentration of a specific gas in the measurement object gas, and may include a reference electrode that is formed inside the layered body, and that is exposed to the reference gas introduced thereto through the reference gas introducing space, and detection means that detects the concentration of the specific gas in the measurement object gas on the basis of an electromotive force generated between the reference electrode and the measurement electrode. In such a case, the gas sensor of the present invention may include an outer electrode disposed on an outer surface of the layered body, and the detection means may be means that pumps out or pumps in oxygen through the measurement electrode and the outer electrode in accordance with an electromotive force generated between the reference electrode and the measurement electrode, and that detects the concentration of the specific gas in the measurement object gas on the basis of a current flowing upon the pumping-out or the pumping-in of oxygen.

DETAILED DESCRIPTION OF THE INVENTION

Figure 1A:
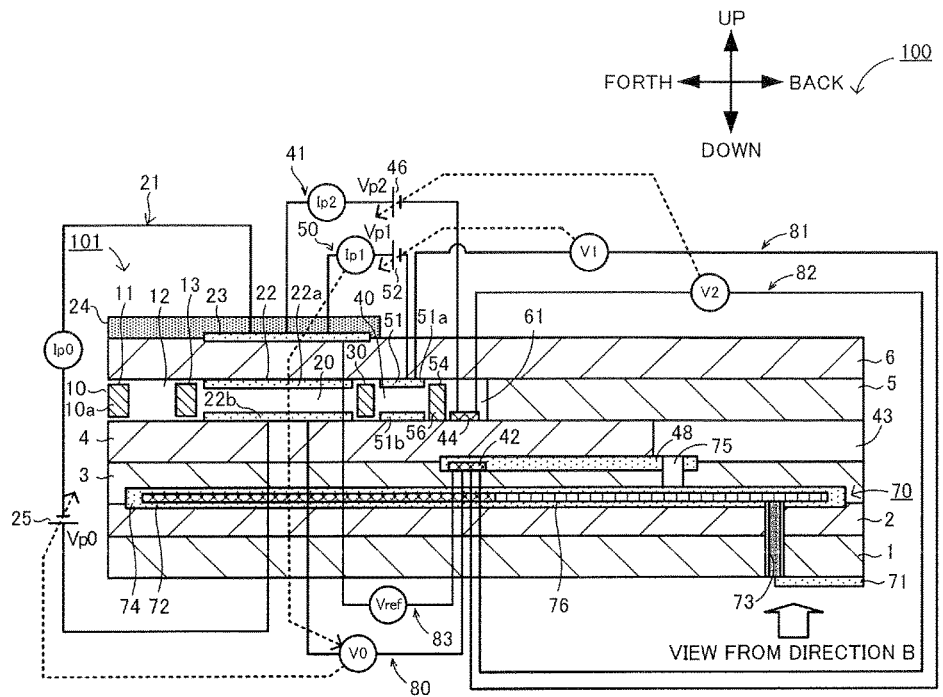
FIG. 1A and FIG. 1B are schematic sectional views of a gas sensor 100.
Figure 1B:
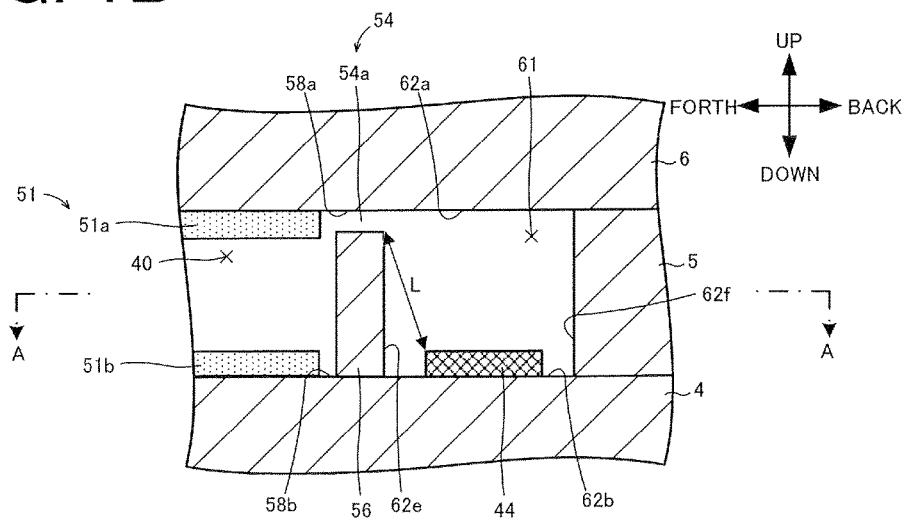
Figure 2:
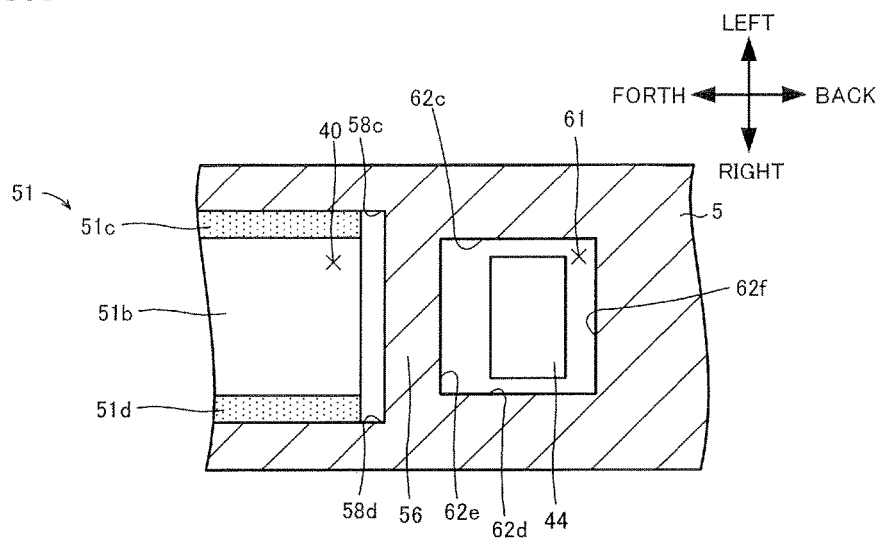
FIG. 2 is a sectional view taken along A-A in FIG. 1B.

A basic structure of a gas sensor 100 including a sensor element 101, according to an exemplary embodiment of the present invention, will be described below. FIG. 1A and FIG. 1E are schematic sectional views of a gas sensor 100 illustrating, in a simplified fashion, one example of a structure of the gas sensor 100. FIG. 1A is a schematic sectional view of the gas sensor 100, and FIG. 1B is an enlarged view of a region in FIG. 1A around a measurement electrode 44 and a third inner cavity 61. FIG. 2 is a sectional view taken along A-A in FIG. 1B. The gas sensor 100 includes the sensor element 101 that detects the concentration of a specific gas (NOx in this embodiment) in measurement object gas. The sensor element 101 has an elongate rectangular parallelepiped shape. It is assumed that a lengthwise direction of the sensor element 101 (right and left direction in FIG. 1) is defined as a back and forth direction, and a direction of thickness of the sensor element 101 (up and down direction in FIG. 1) is defined as an up and down direction. Furthermore, a widthwise direction of the sensor element 101 (direction perpendicular to both the back and forth direction and the up and down direction) is defined as a right and left direction (up and down direction in FIG. 2).

The sensor element 101 is an element including a layered body in which six layers, i.e., a first substrate layer 1, a second substrate layer 2, a third substrate layer 3, a first solid electrolyte layer 4, a spacer layer 5, and a second solid electrolyte layer 6, those layers being each a layer made of an ion-conductive solid electrolyte, such as zirconia ($ZrO_2$), are successively stacked in the mentioned order from the lower side when viewed on the drawing. The solid electrolyte forming each of those six layers is a dense and gas-tight substance. The sensor element 101 is manufactured, for example, by carrying out predetermined processing, printing of a circuit pattern, etc. on ceramic green sheets corresponding to the six layers, respectively, stacking those ceramic green sheets, and then firing the stacked sheets into an integral body. Though not illustrated, an adhesive layer (not illustrated) is present between every two of the layers 1 to 6, and the adjacent layers in the up and down direction are bonded to each other with the adhesive layer interposed therebetween.

In one end portion of the sensor element 101 (left side in FIG. 1) and between a lower surface of the second solid electrolyte layer 6 and an upper surface of the first solid electrolyte layer 4, a gas inlet 10, a first diffusion rate-controlling portion 11, a buffer space 12, a second diffusion rate-controlling portion 13, a first inner cavity 20, a third diffusion rate-controlling portion 30, a second inner cavity 40, a fourth diffusion rate-controlling portion 54, and a third inner cavity 61 are successively formed adjacent to each other in the mentioned order in a thoroughly communicating state.

The gas inlet 10, the buffer space 12, the first inner cavity 20, the second inner cavity 40, and the third inner cavity 61 are each an inner space of the sensor element 101, which is formed by boring the spacer layer 5, and which is defined at its top by the lower surface of the second solid electrolyte layer 6, at its bottom by the upper surface of the first solid electrolyte layer 4, and at its sides by lateral surfaces of the spacer layer 5.

The first diffusion rate-controlling portion 11, the second diffusion rate-controlling portion 13, and the third diffusion rate-controlling portion 30 are each provided as two horizontally-elongate slits (each having an opening with a lengthwise direction thereof being a direction perpendicular to the drawing). Though described in detail later, the fourth diffusion rate-controlling portion 54 is provided as one horizontally-elongate slit (having an opening with a lengthwise direction thereof being the direction perpendicular to the drawing). A region spanning from the gas inlet 10 to the third inner cavity 61 is also called a measurement-object gas flowing portion. The measurement object gas flows through the measurement-object gas flowing portion from the front side toward the rear side.

At a location farther away from the one end side of the sensor element 101 than the measurement-object gas flowing portion, a reference gas introducing space 43 is formed at a position between an upper surface of the third substrate layer 3 and a lower surface of the spacer layer 5, and is defined at its sides by lateral surfaces of the first solid electrolyte layer 4. For example, the atmosphere is introduced to the reference gas introducing space 43 as reference gas when the concentration of NOx is measured.

An atmosphere introducing layer 48 is a layer that is made of a ceramic, such as porous alumina, and that is exposed to the reference gas introducing space 43. The reference gas is introduced to the atmosphere introducing layer 48 through the reference gas introducing space 43. Furthermore, the atmosphere introducing layer 48 is formed in covering relation to a reference electrode 42. The atmosphere introducing layer 48 introduces the reference gas to the reference electrode 42 while giving predetermined diffusion resistance to the reference gas in the reference gas introducing space 43.

The reference electrode 42 is an electrode that is formed in a state sandwiched between the upper surface of the third substrate layer 3 and the first solid electrolyte layer 4. As described above, the atmosphere introducing layer 48 communicating with the reference gas introducing space 43 is disposed around the reference electrode 42. The reference electrode 42 is formed directly on the upper surface of the third substrate layer 3 and is covered with the atmosphere introducing layer 48 at its surfaces except for the surface in contact with the upper surface of the third substrate layer 3. As described later, oxygen concentration (oxygen partial pressure) in each of the first inner cavity 20, the second inner cavity 40, and the third inner cavity 61 can be measured by employing the reference electrode 42.

In the measurement-object gas flowing portion, the gas inlet 10 provides a region opened to an external space, and the measurement object gas is taken into the sensor element 101 from the external space through the gas inlet 10. The first diffusion rate-controlling portion 11 serves as a region for giving predetermined diffusion resistance to the measurement object gas that has been taken in through the gas inlet 10. The first diffusion rate-controlling portion 11 is formed as a slit-like gap between an entry partition wall 10a, which is a part of the spacer layer 5, and each of the second solid electrolyte layer 6 and the first solid electrolyte layer 4, which are positioned respectively on the upper and lower sides of the entry partition wall 10a. In this embodiment, a front end of the entry partition wall 10a is at the same position as a front end of the sensor element 101 (i.e., respective front ends of the second solid electrolyte layer 6, the spacer layer 5, and the first solid electrolyte layer 4) in the back-and-forth direction. In other words, the front end of the entry partition wall 10a and the front end of the sensor element 101 are positioned on the same plane. Thus, an opening at the front end of the first diffusion rate-controlling portion 11 serves as the gas inlet 101. The present invention is not limited to such an arrangement. The front end of the partition wall 10a may be positioned rearward of the front end of the sensor element 101, and a space may be present between the gas inlet 10 and the first diffusion rate-controlling portion 11.

The buffer space 12 is a space that is partitioned by the entry partition wall 10a from the outside, and that introduces the measurement object gas, which has been introduced from the first diffusion rate-controlling portion 11, to the second diffusion rate-controlling portion 13. The second diffusion rate-controlling portion 13 serves as a region for giving predetermined diffusion resistance to the measurement object gas that is introduced from the buffer space 12 to the first inner cavity 20. When the measurement object gas is introduced from the outside of the sensor element 101 to the first inner cavity 20, the measurement object gas is abruptly taken into the inside of the sensor element 101 from the gas inlet 10 in accordance with pressure fluctuations of the measurement object gas in the outside space (i.e., with pulsation of exhaust pressure when the measurement object gas is exhaust gas of an automobile). However, the taken-in measurement object gas is not directly introduced to the first inner cavity 20, but it is introduced to the first inner cavity 20 after fluctuations in the concentration of the measurement object gas have been settled through the first diffusion rate-controlling portion 11, the buffer space 12, and the second diffusion rate-controlling portion 13. As a result, the fluctuations in the concentration of the measurement object gas introduced to the first inner cavity 20 are reduced to a substantially negligible level. The first inner cavity 20 is provided as a space for adjusting the partial pressure of oxygen in the measurement object gas that has been introduced through the second diffusion rate-controlling portion 13. The oxygen partial pressure is adjusted with operation of a main pump cell 21.

The main pump cell 21 is an electrochemical pump cell constituted by an inner pump electrode 22 having a ceiling electrode portion 22a that is disposed substantially over the entire lower surface of the second solid electrolyte layer 6 in its region facing the first inner cavity 20, an outer pump electrode 23 disposed on a region of an upper surface of the second solid electrolyte layer 6, the region corresponding to the ceiling electrode portion 22a, in a state exposed to the outside space, and the second solid electrolyte layer 6 sandwiched between those two electrodes.

The inner pump electrode 22 is formed to extend over respective regions of the solid electrolyte layers on the upper and lower sides (i.e., the second solid electrolyte layer 6 and the first solid electrolyte layer 4) and over regions of the spacer layer 5, those regions defining upper and lower walls and both sidewalls of the first inner cavity 20. More specifically, the ceiling electrode portion 22a is formed on the lower surface of the second solid electrolyte layer 6, which provides a ceiling surface of the first inner cavity 20, and a bottom electrode portion 22b is formed directly on the upper surface of the first solid electrolyte layer 4, which provides a bottom surface of the first inner cavity 20. Furthermore, lateral electrode portions (not illustrated) are formed on sidewall surfaces (inner surfaces) of the spacer layer 5, which define both the sidewalls of the first inner cavity 20, to connect the ceiling electrode portion 22a and the bottom electrode portion 22b. Thus, the inner pump electrode 22 is disposed in a tunnel-like structure in a region where the lateral electrode portions are disposed.

The inner pump electrode 22 and the outer pump electrode 23 are each formed as a porous cermet electrode (e.g., a cermet electrode made of Pt and $ZrO_2$ and containing 1% of Au). The inner pump electrode 22 contacting the measurement object gas is made of a material having a reducing ability that is weakened for NOx components in the measurement object gas. In this embodiment, as illustrated in FIG. 1A, a rear end of the inner pump electrode 22 and a rear end of the outer pump electrode 23 are deviated from each other in the back and forth direction such that the rear end of the outer pump electrode 23 is positioned on the more rear side. However, the present invention is not limited to such an arrangement. The rear end of the inner pump electrode 22 and the rear end of the outer pump electrode 23 may be located at the same position in the back and forth direction. Alternatively, the rear end of the outer pump electrode 23 may be positioned forward of the rear end of the inner pump electrode 22.

In the main pump cell 21, oxygen in the first inner cavity 20 can be pumped out to the outer space, or oxygen in the outer space can be pumped into the first inner cavity 20 by applying a desired pump voltage Vp0 between the inner pump electrode 22 and the outer pump electrode 23, thus causing a pump current Ip0 to flow in a positive direction or a negative direction between the inner pump electrode 22 and the outer pump electrode 23.

Furthermore, to detect the oxygen concentration (oxygen partial pressure) in an atmosphere inside the first inner cavity 20, an electrochemical sensor cell, i.e., an oxygen partial-pressure detection sensor cell 80 for controlling a main pump, is constituted by the inner pump electrode 22, the second solid electrolyte layer 6, the spacer layer 5, the first solid electrolyte layer 4, and the reference electrode 42.

The oxygen concentration (oxygen partial pressure) in the first inner cavity 20 can be determined by measuring an electromotive force V0 in the oxygen partial-pressure detection sensor cell 80 for controlling the main pump. Moreover, the pump current Ip0 is controlled by feedback controlling the pump voltage Vp0 given from a variable power supply 25 such that the electromotive force V0 is held constant. As a result, the oxygen concentration in the first inner cavity 20 can be held at a predetermined constant value.

The third diffusion rate-controlling portion 30 serves as a region for applying predetermined diffusion resistance to the measurement object gas of which oxygen concentration (oxygen partial pressure) has been controlled in the first inner cavity 20 with the operation of the main pump cell 21, and for introducing the relevant measurement object gas to the second inner cavity 40.

The second inner cavity 40 is provided as a space where further adjustment of the oxygen partial pressure is performed by an auxiliary pump cell 50 on the measurement object gas that is introduced to the second inner cavity 40 through the third diffusion rate-controlling portion 30 after the adjustment of the oxygen concentration (oxygen partial pressure) in the first inner cavity 20. As a result, the oxygen concentration in the second inner cavity 40 can be held constant with high accuracy, and the gas sensor 100 described above can measure the concentration of NOx with high accuracy.

The auxiliary pump cell 50 is an auxiliary electrochemical pump cell constituted by an auxiliary pump electrode 51 having a ceiling electrode portion 51a, which is disposed substantially over an entire region of the lower surface of the second solid electrolyte layer 6, the region facing the second inner cavity 40, the outer pump electrode 23 (note that a suitable electrode outside the sensor element 101 can be used without being limited to the outer pump electrode 23), and the second solid electrolyte layer 6.

The auxiliary pump electrode 51 is disposed inside the second inner cavity 40 in a tunnel-like structure, which is similar to that of the above-mentioned inner pump electrode 22 disposed inside the first inner cavity 20. More specifically, the ceiling electrode portion 51a is formed in a region of the second solid electrolyte layer 6, the region providing a ceiling surface of the second inner cavity 40, and a bottom electrode portion 51b is formed directly on a region of the upper surface of the first solid electrolyte layer 4, the region providing a bottom surface of the second inner cavity 40. Furthermore, lateral electrode portions 51c and 51d (see FIG. 2) connecting the ceiling electrode portion 51a and the bottom electrode portion 51b are formed respectively on regions of the right and left wall surfaces of the spacer layer 5, the regions defining sidewalls of the second inner cavity 40. Thus, the auxiliary pump electrode 51 has a tunnel-like structure including the ceiling electrode portion 51a, the bottom electrode portion 51b, and the lateral electrode portions 51c and 51d. In this embodiment, positions and shapes of the ceiling electrode portion 51a and the bottom electrode portion 51b formed as described above are symmetrical in the up and down direction. However, the present invention is not limited to such an arrangement, and the ceiling electrode portion 51a and the bottom electrode portion 51b may be arranged in asymmetric relation. Furthermore, positions and shapes of the lateral electrode portion 51c and the lateral electrode portion 51d formed described above are preferably symmetrical in the right and left direction. However, the present invention is not limited to such an arrangement, and the lateral electrode portion 51c and the lateral electrode portion 51d are just required to electrically connect the ceiling electrode portion 51a and the bottom electrode portion 51b. Similarly to the inner pump electrode 22, the auxiliary pump electrode 51 is made of a material having a reducing ability that is weakened for NOx components in the measurement object gas.

In the auxiliary pump cell 50, oxygen in an atmosphere inside the second inner cavity 40 can be pumped out to the outer space, or oxygen can be pumped into the second inner cavity 40 from the outer space by applying a desired pump voltage Vp1 between the auxiliary pump electrode 51 and the outer pump electrode 23.

Furthermore, to control the oxygen partial pressure in an atmosphere inside the second inner cavity 40, an electrochemical sensor cell, i.e., an oxygen partial-pressure detection sensor cell 81 for controlling an auxiliary pump, is constituted by the auxiliary pump electrode 51, the reference electrode 42, the second solid electrolyte layer 6, the spacer layer 5, and the first solid electrolyte layer 4.

The auxiliary pump cell 50 performs pumping with the aid of a variable power supply 52 of which voltage is controlled in accordance with an electromotive force V1 detected by the oxygen partial-pressure detection sensor cell 81 for controlling the auxiliary pump. As a result, the oxygen partial pressure in the atmosphere inside the second inner cavity 40 can be controlled to a low level of partial pressure at which the measurement of NOx is substantially not affected.

In addition, a pump current Ip1 from the variable power supply 52 is used to control the electromotive force of the oxygen partial-pressure detection sensor cell 80 for controlling the main pump. More specifically, the pump current Ip1 is input as a control signal to the oxygen partial-pressure detection sensor cell 80 for controlling the main pump, in order to control the electromotive force V0 thereof. As a result, a gradient of the oxygen partial pressure in the measurement object gas introduced from the third diffusion rate-controlling portion 30 to the second inner cavity 40 is controlled to be always held constant. When the sensor element is used as a NOx sensor, the oxygen concentration in the second inner cavity 40 is held at a constant value of about 0.001 ppm with operations of the main pump cell 21 and the auxiliary pump cell 50.

The fourth diffusion rate-controlling portion 54 serves as a flow path for applying predetermined diffusion resistance to the measurement object gas of which oxygen concentration (oxygen partial pressure) has been controlled in the second inner cavity 40 with the operation of the auxiliary pump cell 50, and for introducing the relevant measurement object gas to the third inner cavity 61. The fourth diffusion rate-controlling portion 54 has a role to limit an amount of NOx flowing into the third inner cavity 61. As illustrated in FIG. 1B, the fourth diffusion rate-controlling portion 54 includes a diffusion rate-controlling portion 54a. The diffusion rate-controlling portion 54a is formed as a slit defined by a partition wall 56, which is a part of the spacer layer 5, and upper one 58a (i.e., a ceiling surface defined by the lower surface of the second solid electrolyte layer 6) of upper, lower, left, and right inner peripheral surfaces (i.e., an upper surface 58a, a lower surface 58b, a left surface 58c, and a right surface 58d) of the measurement-object gas flowing portion. A height of the opening of the diffusion rate-controlling portion 54a in the up and down direction (i.e., a distance between the partition wall 56 and the upper surface 58a) is, e.g., 0.03 mm or less, though not being particularly limited to such a value. As illustrated in FIG. 2, the partition wall 56 is formed as a portion of the spacer layer 5 between the second inner cavity 40 and the third inner cavity 61, which are formed by boring the spacer layer 5. The right and left sides of the partition wall 56 are joined to other portions of the spacer layer 5, and any gaps allowing the measurement object gas to flow therethrough are not present at the right and left sides of the partition wall 56. Furthermore, the lower surface of the partition wall 56 and the lower surface 58b of the measurement-object gas flowing portion (i.e., the upper surface of the first solid electrolyte layer 4) are bonded to each other with the above-mentioned adhesive layer (not illustrated) interposed between them. Hence any gap allowing the measurement object gas to flow therethrough is not present at the lower side of the partition wall 56.

The third inner cavity 61 is a space partitioned by the partition wall 56 from the second inner cavity 40 at the inflow side of the measurement object gas. The third inner cavity 61 is provided as a space where processing to measure the concentration of nitrogen oxides (NOx) in the measurement object gas is performed on the measurement object gas introduced through the fourth diffusion rate-controlling portion 54 after the oxygen concentration (oxygen partial pressure) has been previously adjusted in the second inner cavity 40. The measurement of the NOx concentration is mainly performed in the third inner cavity 61 with operation of a measurement pump cell 41. In this embodiment, as illustrated in FIG. 2, a width of the third inner cavity 61 in the right and left direction is smaller than that of the second inner cavity 40. However, the present invention is not limited to such an example. The widths of the third inner cavity 61 and the second inner cavity 40 in the right and left direction may be the same, or the width of the third inner cavity 61 in the right and left direction may be larger. The third inner cavity 61 has a length of, e.g., 0.4 mm to 1 mm in the back and forth direction, a height of, e.g., 0.05 mm to 0.3 mm in the up and down direction, and a width of, e.g., 1 mm to 3 mm in the right and left direction, though not being particularly limited to those values.

The measurement pump cell 41 measures, inside the third inner cavity 61, the concentration of NOx in the measurement object gas. The measurement pump cell 41 is an electrochemical pump cell that is constituted by the measurement electrode 44, the outer pump electrode 23, the second solid electrolyte layer 6, the spacer layer 5, and the first solid electrolyte layer 4. The measurement electrode 44 is a porous cermet electrode. The measurement electrode 44 also functions as a NOx reducing catalyst for reducing NOx that is present in an atmosphere inside the third inner cavity 61. The measurement electrode 44 is formed directly on lower one 62b (i.e., a bottom surface defined by the upper surface of the first solid electrolyte layer 4) of upper, lower, left, right, front and rear inner peripheral surfaces (i.e., an upper surface 62a, a lower surface 62b, a left surface 62c, a right surface 62d, a front surface 62e, and a rear surface 62f) of the third inner cavity 61. In other words, the measurement electrode 44 is formed directly on the lower surface 62b positioned on the side opposite to the upper surface 58a along which the fourth diffusion rate-controlling portion 54 (i.e., the diffusion rate-controlling portion 54a) is formed. The surface of the measurement electrode 44 is exposed to the third inner cavity 61. A distance L (see FIG. 1B) between the diffusion rate-controlling portion 54a and the measurement electrode 44 is preferably 0.1 mm or more. A thickness of the measurement electrode 44 is 0.03 mm or less, for example, though not being particularly limited to those values.

In the measurement pump cell 41, oxygen generated through decomposition of the nitrogen oxides in an atmosphere around the measurement electrode 44 can be pumped out, and an amount of the generated oxygen can be detected as a pump current Ip2.

To detect the oxygen partial pressure around the measurement electrode 44, an electrochemical sensor cell, i.e., an oxygen partial-pressure detection sensor cell 82 for controlling a measurement pump, is constituted by the first solid electrolyte layer 4, the measurement electrode 44, and the reference electrode 42. A variable power supply 46 is controlled in accordance with an electromotive force V2 that is detected by the oxygen partial-pressure detection sensor cell 82 for controlling the measurement pump.

The measurement object gas introduced to the second inner cavity 40 reaches the measurement electrode 44 in the third inner cavity 61 through the fourth diffusion rate-controlling portion 54 under the condition of the oxygen partial pressure being controlled. The nitrogen oxides in the measurement object gas around the measurement electrode 44 is reduced ($2NO \rightarrow N_2+O_2$), thereby generating oxygen. The generated oxygen is subjected to pumping by the measurement pump cell 41. At that time, a voltage Vp2 of the variable power supply 46 is controlled such that the control voltage V2 detected by the oxygen partial-pressure detection sensor cell 82 for controlling the measurement pump is held constant. Because the amount of oxygen generated around the measurement electrode 44 is in proportion to the concentration of the nitrogen oxides in the measurement object gas, the concentration of the nitrogen oxides in the measurement object gas is calculated by employing the pump current Ip2 in the measurement pump cell 41.

As an alternative, the measurement electrode 44, the first solid electrolyte layer 4, the third substrate layer 3, and the reference electrode 42 may be combined to constitute an electrochemical sensor cell that serves as an oxygen partial pressure detection means. The oxygen partial pressure detection means can detect an electromotive force depending on a difference between an amount of oxygen generated with reduction of NOx components, which are present in the atmosphere around the measurement electrode 44, and an amount of oxygen contained in the atmosphere as a reference. Accordingly, the concentration of the NOx components in the measurement object gas can be determined from the detected electromotive force.

In addition, an electrochemical sensor cell 83 is constituted by the second solid electrolyte layer 6, the spacer layer 5, the first solid electrolyte layer 4, the third substrate layer 3, the outer pump electrode 23, and the reference electrode 42. The oxygen partial pressure in the measurement object gas outside the gas sensor can be detected from an electromotive force Vref that is obtained by the sensor cell 83.

In the gas sensor 100 constituted as described above, the measurement object gas having the oxygen partial pressure, which is always held at a low constant value (i.e., a value substantially not affecting the measurement of NOx), is applied to the measurement pump cell 41 by operating the main pump cell 21 and the auxiliary pump cell 50. Thus, the concentration of NOx in the measurement object gas can be determined on the basis of the pump current Ip2 that flows upon pumping-out of oxygen by the measurement pump cell 41, the oxygen being generated with reduction of NOx substantially in proportion to the concentration of NOx in the measurement object gas.

In order to increase the oxygen ion conductivity of the solid electrolyte, the sensor element 101 further includes a heater section 70 having a role of temperature adjustment to heat the sensor element 101 and to hold its temperature. The heater section 70 includes a heater connector electrode 71, a heater 72, a through-hole 73, a heater insulating layer 74, a pressure release hole 75, and lead lines 76.

Figure 3:
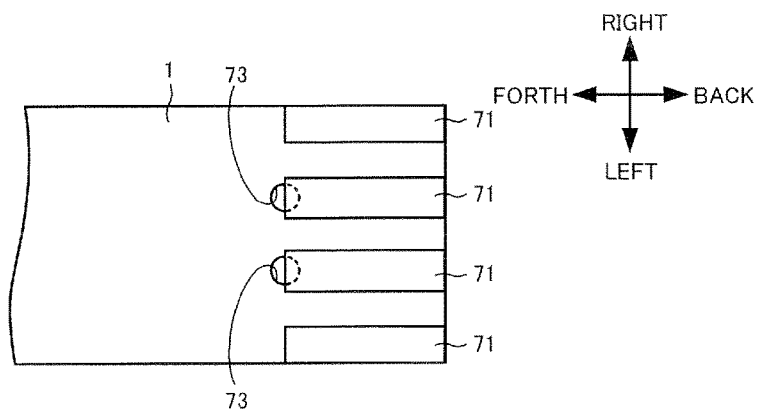
FIG. 3 is a partial view when viewed from a direction denoted by B in FIG. 1A.

The heater connector electrode 71 is an electrode formed in a state contacting a lower surface of the first substrate layer 1. By connecting the heater connector electrode 71 to an external power supply, electric power can be supplied to the heater section 70 from the outside. As illustrated in FIG. 3, the heater connector electrode 71 is formed plural (four in this embodiment) on the lower surface of the first substrate layer 1. A width of each heater connector electrode 71 in the right and left direction is preferably 0.6 mm or less. As a result, a distance between the heater connector electrodes 71 in the right and left direction can be set relatively large, and a leak current between the heater connector electrodes 71 can be suppressed more reliably. Furthermore, in this embodiment, two central ones of the heater connector electrodes 71 in the right and left direction are each connected to the through-hole 73. As illustrated in FIG. 3, a diameter of the through-hole 73 is preferably smaller than the width of the heater connector electrode 71 in the right and left direction, which is connected to the through-hole 73. For example, a conductive material having the same material properties as those of the heater connector electrode 71 is filled in the through-hole 73.

The heater 72 is an electrical resistor formed in a state sandwiched between the second substrate layer 2 and the third substrate layer 3 from below and above, respectively. The heater 72 is connected to the heater connector electrodes 71 via the lead lines 76 and the through-holes 73. The heater 72 generates heat with supply of electric power from the outer side through the heater connector electrodes 71, thereby heating the solid electrolytes constituting the sensor element 101 and holding temperatures thereof.

Moreover, the heater 72 is embedded in a state extending over an entire region from the first inner cavity 20 to the third inner cavity 61 such that the sensor element 101 can be entirely controlled to a temperature at which the solid electrolytes are activated.

The heater insulating layer 74 is an insulating layer made of porous alumina, which is formed to cover upper and lower surfaces of the heater 72 by employing an insulator made of alumina, for example. The heater insulating layer 74 is formed with intent to ensure electrical insulation between the second substrate layer 2 and the heater 72 and electrical insulation between the third substrate layer 3 and the heater 72.

The pressure release hole 75 is formed in a state penetrating through the third substrate layer 3 and communicating with the reference gas introducing space 43, and it is provided with intent to relieve a rise of inner pressure attributable to a temperature rise within the heater insulating layer 74.

Moreover, as illustrated in FIG. 1A, the sensor element 101 includes a porous protective layer 24 covering the outer pump electrode 23. The porous protective layer 24 covers a region of an upper surface of the sensor element 101 (specifically, a region of the upper surface of the second solid electrolyte layer 6), the region extending from a front end of the relevant upper surface to a position rearward of a rear end of the outer pump electrode 23. The porous protective layer 24 is made of a porous body, such as an alumina porous body, a spinel porous body, a cordierite porous body, a titania porous body, or a magnesia porous body. The porous protective layer 24 has a role to suppress the outer pump electrode 23 from being deteriorated by hydrocarbons (HC), CO, $CO_2$, etc. in the measurement object gas, and to avoid peeling-off of the outer pump electrode 23 from the second solid electrolyte layer 6. A thickness of the porous protective layer 24 is preferably twice or more that of the outer pump electrode 23. As a result, the effect of avoiding the peeling-off of the outer pump electrode 23 can be increased.

One example of a method for manufacturing the above-described sensor element 101 of the gas sensor 100 will be described below. First, six unfired ceramic green sheets are prepared each of which contains, as a ceramic component, an oxygen ion-conductive solid electrolyte, such as zirconia. Each green sheet has a plurality of sheet holes used for positioning in steps of printing and stacking, a plurality of necessary through-holes, etc., which are formed therein in advance. Furthermore, in the green sheet becoming the spacer layer 5, a space serving as the measurement-object gas flowing portion is formed in advance by punching, for example. Similarly, in the green sheet becoming the first solid electrolyte layer 4, a space serving as the reference gas introducing space 43 is formed in advance. A pattern printing process and a drying process are then performed to form various patterns on the ceramic green sheets corresponding to the first substrate layer 1, the second substrate layer 2, the third substrate layer 3, the first solid electrolyte layer 4, the spacer layer 5, and the second solid electrolyte layer 6, respectively. More specifically, the patterns formed in those processes are, for example, patterns for the above-mentioned electrodes, the lead lines connected to the electrodes, the atmosphere introducing layer 48, the heater section 70, the porous protective layer 24, and so on. The pattern printing is performed by coating a pattern forming paste, which is prepared depending on characteristics required for each of objective patterns to be formed, over the corresponding green sheet by utilizing the known screen printing technique. The drying process is also performed by employing a known drying means. After the end of the pattern printing and the drying, an adhesive paste for bonding the green sheets, which correspond to the individual layers of the sensor element, in a stacked state is printed over each of the green sheets and then dried. The green sheets including the adhesive pastes formed thereon are successively stacked in a predetermined order through positioning with the aide of the sheet holes, and are then subjected to a press-bonding process of press-bonding the stacked green sheets into a layered body under application of predetermined temperature and pressure. The layered body thus obtained includes the plurality of sensor elements 101. The layered body is cut per unit size of the sensor element 101. Each cut piece of the layered body is fired at a predetermined firing temperature, whereby the sensor element 101 is obtained. After obtaining the sensor element 101 as described above, the sensor element 101 is placed into a predetermined housing and is assembled into a body (not illustrated) of the gas sensor 100, whereby the gas sensor 100 is obtained.

The fourth diffusion rate-controlling portion 54 (the diffusion rate-controlling portion 54a) can be formed, for example, as follows. First, in the above-described pattern printing process, an evaporative material (e.g., theobromine), which is lost through evaporation upon firing, is coated on an upper surface of a part of the green sheet corresponding to the spacer layer 5, the part becoming the partition wall 56. The evaporative material is lost during the above-mentioned firing, and a gap is formed between the upper surface of the partition wall 56 as a part of the spacer layer 5 and the upper surface 58a of the gas flowing portion (i.e., the lower surface of the second solid electrolyte layer 6), the gap serving as the diffusion rate-controlling portion 54a. The evaporative material may be coated on not only the part becoming the partition wall 56, but also on a region of a lower surface of the green sheet becoming the second solid electrolyte layer 6, the region being positioned opposite to the partition wall 56. A height of the diffusion rate-controlling portion 54a in the up and down direction can be adjusted by adjusting a thickness of the coated evaporative material. The first to third diffusion rate-controlling portions 11, 13 and 30 can also be formed in a similar manner except for coating the evaporative material on each of the upper and lower surfaces of the spacer layer 5. It is to be noted that the above-mentioned method for forming the diffusion rate-controlling portion is known in the art and is disclosed in Japanese Patent No. 4911910, for example.

The filling of the conductive material into the through-hole 73 can be performed by the known through-hole printing, for example. More specifically, in the pattern printing process, a pattern made of a conductive paste and becoming the heater connector electrode 71 illustrated in FIGS. 1 and 3 is formed, by screen printing, on a lower surface of the green sheet that becomes the first substrate layer 15. Then, the through-hole 73 is brought into a condition of negative pressure at the side opposite to the formed pattern (i.e., at the upper surface side of the green sheet becoming the first substrate layer 1), thus causing a part of the screen-printed conductive paste to flow into the through-hole 73 to be filled in the through-hole 73. By performing the through-hole printing in such a manner, the inside of the through-hole 73 after the firing is filled with the conductive material, and the heater connector electrode 71 is electrically connected to the heater lead line 76. By setting the diameter of the through-hole 73 to be smaller than the width of the heater connector electrode 71, which is to be connected, in the right and left direction as described above, the conductive paste printed on a portion becoming the heater connector electrode 71 is caused to more easily flow into the through-hole 73. As a result, the heater connector electrode 71 and the heater lead line 76 can be electrically connected via the through-hole 73 with higher reliability.

Though not formed in this embodiment, a pattern serving as a warping preventive layer, which has the same shape and is made of the same material as those of the porous protective layer 24, may be formed in the pattern printing process on a region of the lower surface of the sensor element 101, the region being symmetrical to the porous protective layer 24 in the up and down direction. In other words, the pattern becoming the warping preventive layer may be formed on a lower surface of the green sheet becoming the first substrate layer 1. As a result, warping of the layered body is suppressed which is attributable to contraction of the porous protective layer 24 during the firing of the layered body.

In the gas sensor 100 described above, the fourth diffusion rate-controlling portion 54 (the diffusion rate-controlling portion 54a) is formed along the upper surface 58a of the upper, lower, left and right inner peripheral surfaces of the measurement-object gas flowing portion. The measurement electrode 44 is formed on the lower surface 62b of the upper, lower, left and right inner peripheral surfaces of the third inner cavity 61, the lower surface 62b being positioned in orientation different from the upper surface 58a along which the diffusion rate-controlling portion 54 is formed. With such an arrangement, reduction in sensitivity of the measurement electrode can be suppressed. That point will be described in detail below.

Figure 4:
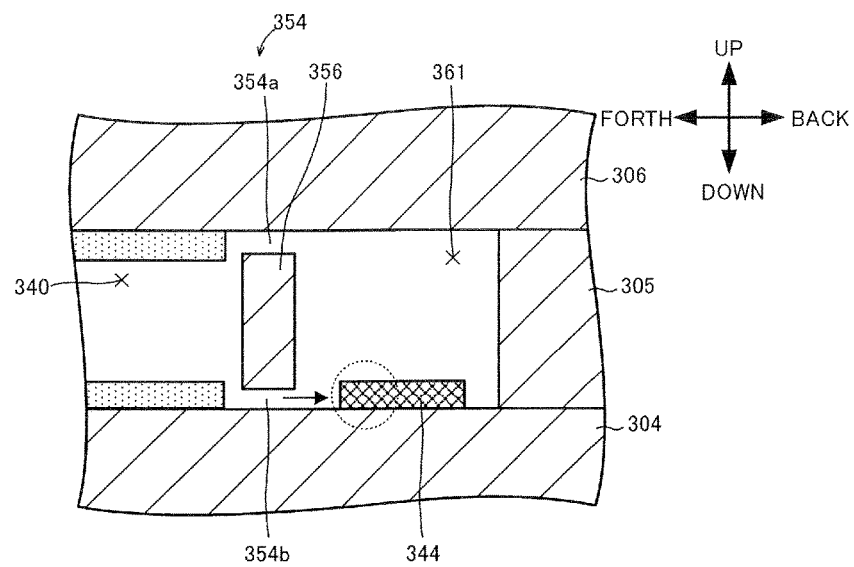
FIG. 4 is an enlarged sectional view of the measurement electrode 344 and thereabout in the related-art gas sensor 300.
Figure 15:
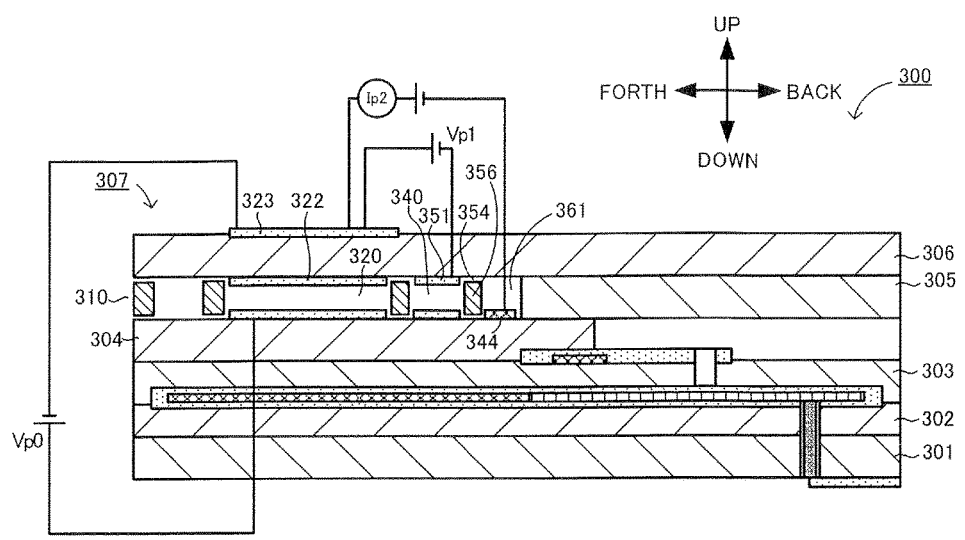
FIG. 15 is a schematic sectional view of the related-art gas sensor 300.

FIG. 4 is an enlarged sectional view of the measurement electrode 344 and thereabout in the related-art gas sensor 300 illustrated in FIG. 15. Of the diffusion rate-controlling portions 354, the diffusion rate-controlling portion formed between the upper surface of the measurement-object gas flowing portion and the partition wall 356 is referred to as a diffusion rate-controlling portion 354a, and the diffusion rate-controlling portion formed between the lower surface of the measurement-object gas flowing portion and the partition wall 356 is referred to as a diffusion rate-controlling portion 354b. As illustrated in FIG. 4, the surface where the diffusion rate-controlling portion 354b is formed (i.e., the lower surface of the measurement-object gas flowing portion and the upper surface of the first solid electrolyte layer 304) and the surface where the measurement electrode 344 is formed (i.e., the lower surface of the third inner cavity 361 and the upper surface of the first solid electrolyte layer 304) are positioned in the same orientation in the up and down direction and in the right and left direction. In such a case, the measurement object gas passing through the diffusion rate-controlling portion 354b tends to flow toward the measurement electrode 344 along the lower surface of the measurement-object gas flowing portion on which the diffusion rate-controlling portion 354b is formed (see an arrow in FIG. 4). Therefore, a portion of the measurement electrode 344, which is positioned nearer to its end on the same side as the diffusion rate-controlling portion 354b, tends to be exposed to the measurement object gas having higher concentration with higher possibility. Stated in another way, a portion of the measurement electrode 344 closer to its front end in FIG. 4 (e.g., a portion surrounded by a dotted line in FIG. 4) tends to be exposed to the measurement object gas having higher concentration with higher possibility. As a result, the front end of the measurement electrode 344 and its portion near the front end mainly fulfill the function as the measurement electrode 344, and currents, such as the pump current Ip2, flow through such an end region in a concentrated fashion. In the end region of the measurement electrode 344 where the currents flow in a larger amount, particles constituting the electrode are more likely to disintegrate into finer particles and to deteriorate. Hence deterioration of the measurement electrode 344 also progresses in the above-mentioned region in a concentration fashion. Accordingly, the sensitivity of the measurement electrode 344 is more apt to reduce. If the measurement electrode 344 deteriorates, the function (catalyst activity) of the measurement electrode 344 as a NOx reduction catalyst is degraded, whereby an amount of oxygen generated through decomposition of nitrogen oxides is reduced, or a resistance value of the measurement electrode 344 is increased. This presumably results in that the pump current Ip2 becomes harder to flow, and that the sensitivity of the measurement electrode 344 is reduced.

Figure 5:
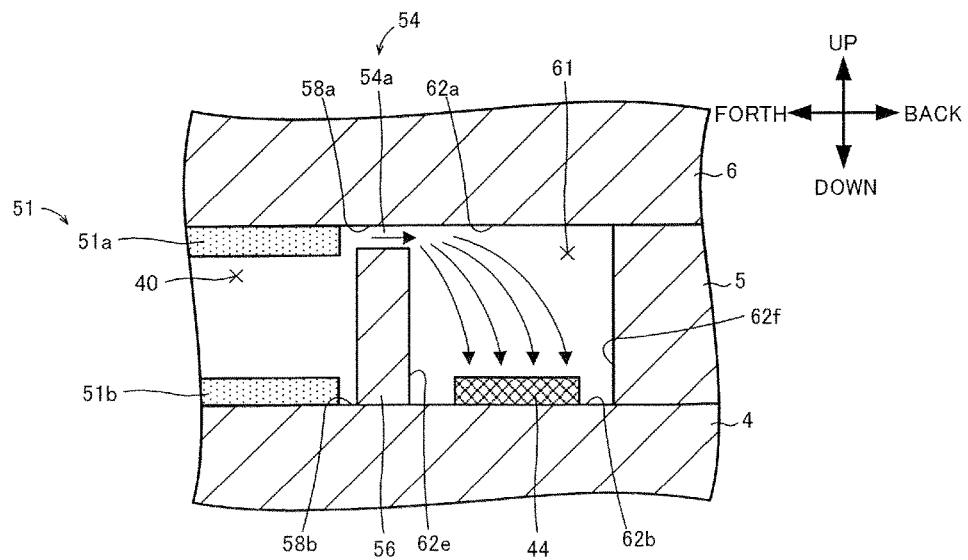
FIG. 5 is an illustration to explain flow of measurement object gas toward a measurement electrode 44.

On the other hand, in the gas sensor 100 of this embodiment, as illustrated in FIG. 5, the measurement electrode 44 and the diffusion rate-controlling portion 54a are formed on and along the surfaces different in orientation in the up and down direction and in the right and left direction, and the diffusion rate-controlling portion is not present in a plane positioned in alignment with a plane where the measurement electrode 44 is present. With such an arrangement, the measurement object gas having passed through the diffusion rate-controlling portion 54a reaches the measurement electrode 44 after having diffused in the third inner cavity 61 (see arrows in FIG. 5). Accordingly, the concentration of the measurement object gas contacting the measurement electrode 44 is less likely to become uneven, for example, between the (front) side closer to the diffusion rate-controlling portion 54a and the (rear) side opposite to the former. As a result, the measurement electrode 44 can more reliably fulfill the function as a measurement electrode in its entirety, and a portion where the pump current Ip2, etc. flow in a concentrated fashion is less likely to occur in the measurement electrode 44. Hence deterioration of the measurement electrode 44 progresses moderately as a whole. Comparing with the case where the diffusion rate-controlling portion 354 and the measurement electrode 344 are formed along and on the surfaces positioned in the same direction (orientation) as illustrated in FIG. 4, therefore, the reduction in sensitivity of the measurement electrode 44 can be further suppressed. In FIG. 4, there is also present the diffusion rate-controlling portion 354a that is formed along the upper surface of the measurement-object gas flowing portion similarly to the diffusion rate-controlling portion 54a. Accordingly, the measurement object gas having passed through the diffusion rate-controlling portion 354a also reaches the measurement electrode 344 after having diffused in the third inner cavity 361 as in the case of FIG. 5. However, because the measurement object gas tends to pass through the diffusion rate-controlling portion 354b as described above, the tendency of the front end of the measurement electrode 344 and its portion near the front end being more likely to deteriorate is not changed in spite of the presence of the diffusion rate-controlling portion 354a.

Correspondence relation between components in this embodiment and components in the present invention is clarified here. The first substrate layer 1, the second substrate layer 2, the third substrate layer 3, the first solid electrolyte layer 4, the spacer layer 5, and the second solid electrolyte layer 6 in this embodiment correspond to a layered body in the present invention. The partition wall 56 corresponds to a partition wall, and the third inner cavity 61 corresponds to a measurement electrode mounting space. The fourth diffusion rate-controlling portion 54 (the diffusion rate-controlling portion 54a) corresponds to a diffusion rate-controlling portion, and the measurement electrode 44 corresponds to a measurement electrode. Furthermore, the reference gas introducing space 43 corresponds to a reference gas introducing space, the reference electrode 42 corresponds to a reference electrode, the measurement pump cell 41 corresponds to detection means, and the outer pump electrode 23 corresponds to an outer electrode.

According to the sensor element 101 of this embodiment described in detail above, the fourth diffusion rate-controlling portion 54 (the diffusion rate-controlling portion 54a) is formed between one or more and three or less surfaces, e.g., the upper surface 58a, of the upper, lower, left and right inner peripheral surfaces (i.e., the upper surface 58a, the lower surface 58b, the left surface 58c, and the right surface 58d) of the measurement-object gas flowing portion and the partition wall 56. The measurement electrode 44 is formed on the lower surface 62b of the upper, lower, left and right inner peripheral surfaces (i.e., the upper surface 62a, the lower surface 62b, the left surface 62c, and the right surface 62d) of the third inner cavity 61, the lower surface 62b being different in orientation from the surface along which the diffusion rate-controlling portion 54a is formed. With such an arrangement, the reduction in sensitivity of the measurement electrode 44 can be suppressed as described above.

Furthermore, the diffusion rate-controlling portion 54a is formed between one, namely the upper surface 58a, of the upper, lower, left and right inner peripheral surfaces of the measurement-object gas flowing portion and the partition wall 56, and the measurement electrode 44 is formed on the lower surface 62b of the upper, lower, left and right inner peripheral surfaces of the third inner cavity 61, the lower surface 62b being positioned on the side opposite to the surface along which the diffusion rate-controlling portion 54a is formed. Therefore, the diffusion rate-controlling portion 54a and the measurement electrode 44 are positioned farther away from each other in comparison with the case where the measurement electrode 44 is formed on the surface that is different in orientation from the surface along which the diffusion rate-controlling portion 54a is formed, but that is not positioned on the side opposite to the latter surface. Accordingly, the measurement object gas is more apt to diffuse in the third inner cavity 61 before the measurement object gas having passed through the diffusion rate-controlling portion 54a reaches the measurement electrode 44. As a result, the above-described effect of suppressing the reduction in sensitivity of the measurement electrode 44 is further increased. Moreover, the diffusion rate-controlling portion 54a is formed between one, namely the upper surface 58a, of the upper and lower inner peripheral surfaces of the measurement-object gas flowing portion and the partition wall 56, and the measurement electrode 44 is formed on the lower surface 62b of the upper and lower inner peripheral surfaces of the third inner cavity 61, the lower surface 62b being positioned on the side opposite to the surface along which the diffusion rate-controlling portion 54a is formed. Therefore, the diffusion rate-controlling portion 54a and the measurement electrode 44 can be formed more easily than in the case where the diffusion rate-controlling portion 54a and the measurement electrode 44 are formed along on and on the right and left inner peripheral surfaces in opposite relation.

In addition, by setting the distance L between the measurement electrode 44 and the diffusion rate-controlling portion 54 to be 0.1 mm or more, the diffusion rate-controlling portion 54 and the measurement electrode 44 are positioned farther away from each other. Accordingly, the measurement object gas is more apt to diffuse in the third inner cavity 61 before the measurement object gas having passed through the diffusion rate-controlling portion 54 reaches the measurement electrode 44. As a result, the above-described effect of suppressing the reduction in sensitivity of the measurement electrode 44 is increased. If the distance L is too large, a response delay in detection of the NOx concentration, for example, would be more likely to occur. An upper limit of the distance L can be determined, as appropriate, depending on an allowable response delay time. The distance L may be set to 2 mm or less though not being particularly limited to such a value.

It is needless to say that the present invention is in no way limited to the above-described embodiment, and that the present invention can be practiced in various forms as far as not departing from the technical scope of the present invention.

Figure 6:
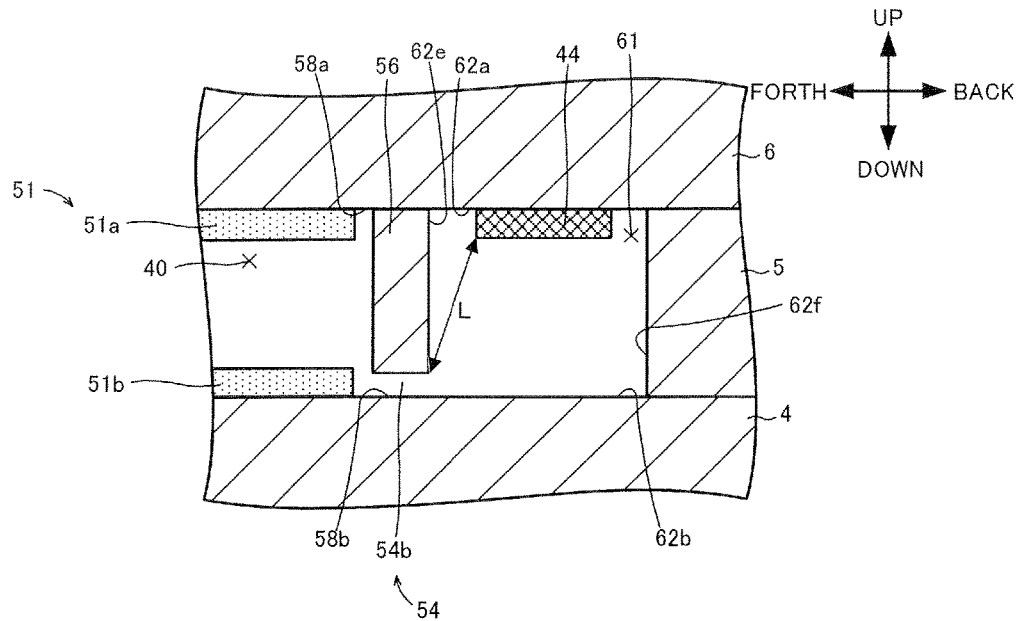
FIG. 6 is an enlarged sectional view of the measurement electrode 44 and thereabout in a sensor element according to a modification.

For example, while, in the above-described embodiment, the diffusion rate-controlling portion 54a is formed along the upper surface 58a of the measurement-object gas flowing portion and the measurement electrode 44 is formed on the lower surface 62b of the third inner cavity 61, the positional relation between the diffusion rate-controlling portion 54a and the measurement electrode 44 may be reversed in the up and down direction. FIG. 6 is an enlarged sectional view of the measurement electrode 44 and thereabout in a sensor element according to a modification that represents the above-mentioned case. FIG. 6 illustrates a section similar to that illustrated in FIG. 1D. In FIG. 6, the fourth diffusion rate-controlling portion 54 includes a diffusion rate-controlling portion 54b instead of the diffusion rate-controlling portion 54a. The diffusion rate-controlling portion 54b is formed between one, namely the lower surface 58b, of the upper, lower, left and right inner peripheral surfaces of the measurement-object gas flowing portion and the partition wall 56. The measurement electrode 44 is formed on the upper surface 62a of the upper, lower, left and right inner peripheral surfaces of the third inner cavity 61, the upper surface 62a being positioned on the side opposite to the surface along which the diffusion rate-controlling portion 54b is formed. Also in such a case, since the surface on which the measurement electrode 44 is formed and the surface along which the diffusion rate-controlling portion 54b is formed are positioned on the sides opposite to each other, the effect of suppressing the reduction in sensitivity of the measurement electrode 44 is increased. Furthermore, since the measurement electrode 44 and the diffusion rate-controlling portion 54b are formed respectively on and along the upper and lower inner peripheral surfaces, the measurement electrode 44 and the diffusion rate-controlling portion 54b can be formed relatively easily.

Figure 7:
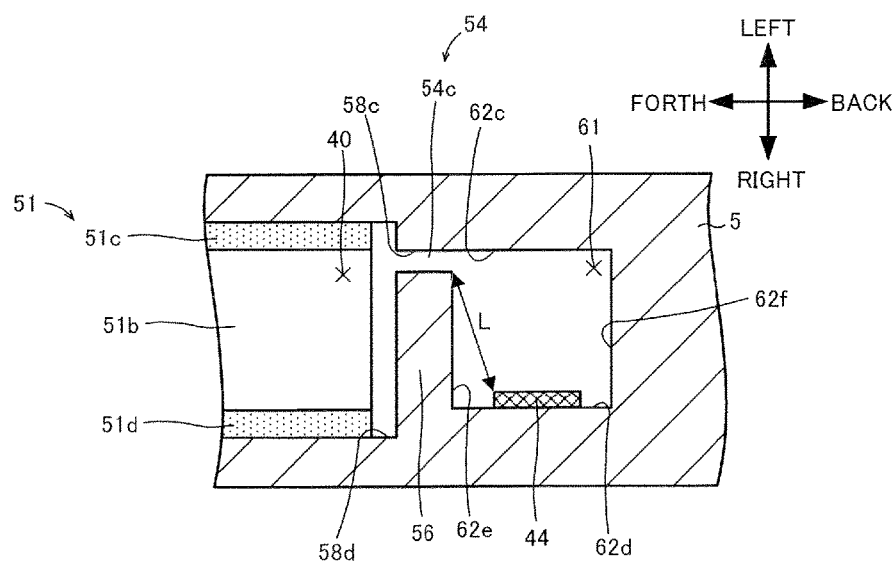
FIG. 7 is an enlarged sectional view of the measurement electrode 44 and thereabout in a sensor element according to a modification.

While, in the above-described embodiment, the diffusion rate-controlling portion 54a and the measurement electrode 44 are formed respectively along and on the upper and lower inner peripheral surfaces, they may be formed along and on the right and left inner peripheral surfaces in opposite relation. FIG. 7 is an enlarged sectional view of the measurement electrode 44 and thereabout in a sensor element according to a modification that represents the above-mentioned case. FIG. 7 illustrates a section similar to that illustrated in FIG. 2. In FIG. 7, the fourth diffusion rate-controlling portion 54 includes a diffusion rate-controlling portion 54c instead of the diffusion rate-controlling portion 54a. The diffusion rate-controlling portion 54c is formed between one, namely the left surface 58c, of the upper, lower, left and right inner peripheral surfaces of the measurement-object gas flowing portion and the partition wall 56. The measurement electrode 44 is formed on the right surface 62d of the upper, lower, left and right inner peripheral surfaces of the third inner cavity 61, the right surface 62d being positioned on the side opposite to the surface along which the diffusion rate-controlling portion 54b is formed. Also in such a case, since the surface on which the measurement electrode 44 is formed and the surface along which the diffusion rate-controlling portion 54c is formed are positioned on the sides opposite to each other, the effect of suppressing the reduction in sensitivity of the measurement electrode 44 is increased. The positional relation between the diffusion rate-controlling portion 54c and the measurement electrode 44 in FIG. 7 may be reversed in the right and left direction. A diffusion rate-controlling portion formed between the right or left inner peripheral surface of the measurement-object gas flowing portion and the partition wall 56, like the diffusion rate-controlling portion 54c, can be formed by punching the green sheet, which becomes the spacer layer 5, in a similar manner to that of forming the third inner cavity 61, etc. In such a case, the evaporative material may be applied in the pattern printing process to a space that has been formed by the punching, and that becomes the diffusion rate-controlling portion. However, the diffusion rate-controlling portion can be formed even without applying the evaporative material. A measurement electrode formed on the right or left inner peripheral surface of the third inner cavity 61, like the measurement electrode 44 in FIG. 7, can be formed by the above-described through-hole printing. More specifically, in the pattern printing process, a paste becoming the measurement electrode 44 is coated by, e.g., screen printing on a region of an upper or lower surface of the green sheet that becomes the spacer layer 5, the region being positioned near a surface on which the measurement electrode 44 is to be formed (i.e., near a surface becoming the right surface 62d in the case of FIG. 7). Then, the surface of the green sheet becoming the spacer layer 5 on the side opposite to the side where the paste has been applied is brought into a condition of negative pressure, thus sucking air in a space becoming the third inner cavity 61 and causing the applied paste to spread over the surface on which the measurement electrode 44 is to be formed (i.e., over the surface becoming the right surface 62d in FIG. 7). As a result, the applied paste is coated over the surface on which the measurement electrode 44 is to be formed. By performing the through-hole printing in such a manner, the measurement electrode 44 is formed on the right surface 62d of the third inner cavity 61 after firing. When the through-hole printing is performed, it is preferable to previously cover, with, e.g., masks, surfaces of the green sheet other than the surface thereof on which the measurement electrode 44 is to be formed (those other surfaces including, among the inner peripheral surfaces (front, rear, left and right surfaces) of the space becoming the third inner cavity 61, the surfaces other than the surface on which the measurement electrode 44 is to be formed, as well as upper and lower surfaces of the green sheet).

While, in the above-described embodiment, the surface on which the measurement electrode 44 is formed and the surface along which the diffusion rate-controlling portion 54a is formed are positioned on the sides opposite to each other, the present invention is not limited to such an example. The measurement electrode 44 is just required to be formed on one of the upper, lower, left and right inner peripheral surfaces of the third inner cavity 61, the one being different in orientation from the surface along which the diffusion rate-controlling portion 54a is formed. For example, in the above-described embodiment, the measurement electrode 44 may be formed on the right surface 62c or the left surface 62d (see FIG. 2). Also in such a case, since the surface on which the measurement electrode 44 is formed and the surface along which the diffusion rate-controlling portion 54a is formed are surfaces different in orientation from each other, the reduction in sensitivity of the measurement electrode 44 can be suppressed.

Figure 8:
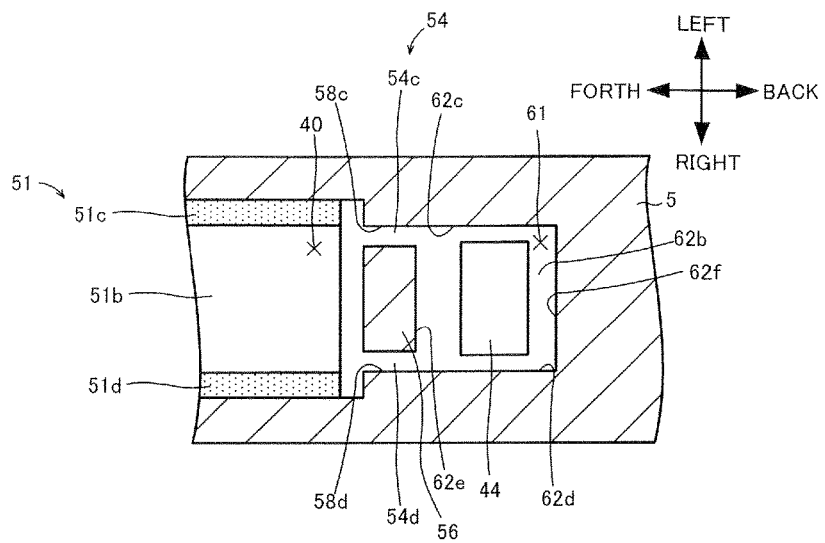
FIG. 8 is an enlarged sectional view of the measurement electrode 44 and thereabout in a sensor element according to a modification.

While, in the above-described embodiment, the fourth diffusion rate-controlling portion 54 includes the diffusion rate-controlling portion 54a formed between one, namely the upper surface 58a, of the upper, lower, left and right inner peripheral surfaces of the measurement-object gas flowing portion and the partition wall 56, the present invention is not limited to such an example. The fourth diffusion rate-controlling portion 54 is just required to include a diffusion rate-controlling portion formed between one or more and three or less surfaces of the upper, lower, left and right inner peripheral surfaces of the measurement-object gas flowing portion and the partition wall 56. FIG. 8 is an enlarged sectional view of the measurement electrode 44 and thereabout in a sensor element according to a modification that represents the above-mentioned case. FIG. 8 illustrates a section similar to that illustrated in FIG. 2. In FIG. 8, the fourth diffusion rate-controlling portion 54 includes, instead of the diffusion rate-controlling portion 54a, a diffusion rate-controlling portion 54c, which is similar to that in FIG. 7, and a diffusion rate-controlling portion 54d. The diffusion rate-controlling portion 54d is formed between one, namely the right surface 58d, of the upper, lower, left and right inner peripheral surfaces of the measurement-object gas flowing portion and the partition wall 56. The measurement electrode 44 is formed on the lower surface 62b of the upper, lower, left and right inner peripheral surfaces of the third inner cavity 61, the lower surface 62b being different in orientation from the surfaces along which the diffusion rate-controlling portions 54c and 54d are formed. Also in such a case, since the surface on which the measurement electrode 44 is formed and the surfaces along which the diffusion rate-controlling portions 54c and 54d are different in orientation from each other, the reduction in sensitivity of the measurement electrode 44 can be suppressed. When the diffusion rate-controlling portions 54c and 54d are both formed as illustrated in FIG. 8, the partition wall 56 is provided as a member separated from the spacer layer 5. When forming the diffusion rate-controlling portions along both the right and left inner peripheral surfaces of the measurement-object gas flowing portion as in the above-mentioned case, it is just required to, after punching the green sheet that becomes the spacer layer 5, coat the evaporative material over at least one of right and left surfaces of the member becoming the partition wall 56 such that the partition wall 56 is bonded through the evaporative material to the green sheet becoming the spacer layer 5.

The fourth diffusion rate-controlling portion 54 may include, without being limited to the modification illustrated in FIG. 8, any one or more and three or less of the diffusion rate-controlling portions 54a to 54d illustrated in FIGS. 1(b) and 6 to 8. For example, when the fourth diffusion rate-controlling portion 54 include the diffusion rate-controlling portions 54a, 54c and 54d, the measurement electrode 44 may be formed on the lower surface 62b that is different in orientation from all of the upper surface 58a, the left surface 58c, and the right surface 58d. It is to be noted that, when the fourth diffusion rate-controlling portion 54 includes a plurality of diffusion rate-controlling portions, the distance between one among the plurality of the diffusion rate-controlling portions, which is closest to the measurement electrode 44, and the measurement electrode 44 is regarded as the distance L.

Figure 9:
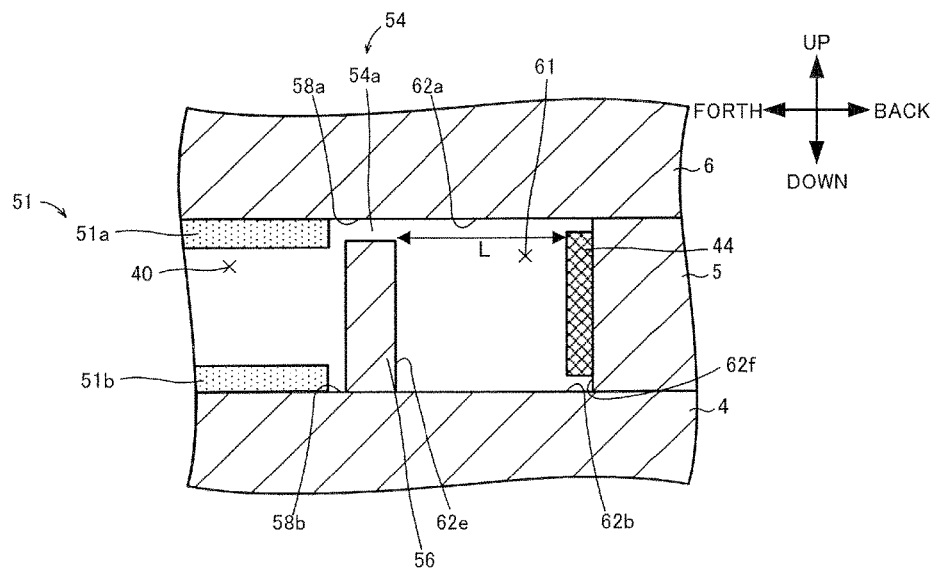
FIG. 9 is an enlarged sectional view of the measurement electrode 44 and thereabout in a sensor element according to a modification.

In the above-described embodiment, insofar as the distance L between the measurement electrode 44 and the fourth diffusion rate-controlling portion 54 is 0.1 mm or more, the measurement electrode 44 may be formed at any position inside the third inner cavity 61. For example, in the above-described embodiment, the measurement electrode 44 may be formed on the upper surface 62a that is positioned in the same direction (orientation) as the upper surface 58a along which the diffusion rate-controlling portion 54a is formed. When the distance L is 0.1 mm or more, the fourth diffusion rate-controlling portion 54 and the measurement electrode 44 are positioned relatively away from each other. Therefore, the measurement object gas is more apt to diffuse in the third inner cavity 61 before the measurement object gas having passed through the fourth diffusion rate-controlling portion 54 reaches the measurement electrode 44. As a result, the reduction in sensitivity of the measurement electrode 44 can be suppressed as in the above-described embodiment. Insofar as the distance L is 0.1 mm or more, the fourth diffusion rate-controlling portion 54 may be formed in any number at any positions. For example, the fourth diffusion rate-controlling portion 54 may include all the diffusion rate-controlling portions 54a to 54d. When the fourth diffusion rate-controlling portion 54 includes all the diffusion rate-controlling portions 54a to 54d, the partition wall 56 may be bonded to or connected (formed integrally) with any of upper and lower solid electrolyte layers (i.e., the first and second solid electrolyte layers 6 and 4) and right and left solid electrolyte layers (i.e., the spacer layer 5) such that the position of the partition wall 56 is fixated. For example, a lower right portion and a lower left portion of the partition wall 56 may be bonded or connected to the spacer layer 5. Alternatively, the diffusion rate-controlling portion may be formed at a position other than between any of the upper, lower, left and right inner peripheral surfaces of the measurement-object gas flowing portion and the partition wall 56, such as represented by the case where the fourth diffusion rate-controlling portion 54 includes a slit-like diffusion rate-controlling portion formed at a center of the partition wall 56 in the up and down direction. Moreover, the measurement electrode 44 may be formed, without being limited to the upper, lower, left and right inner peripheral surfaces of the third inner cavity 61, on the rear surface 62f thereof, which is oriented perpendicularly to the flowing direction of the measurement object gas and positioned on the downstream side in the flowing direction. FIG. 9 is an enlarged sectional view of the measurement electrode 44 and thereabout in a sensor element according to a modification that represents the above-mentioned case. FIG. 9 illustrates a section similar to that illustrated in FIG. 1B. In FIG. 9, the fourth diffusion rate-controlling portion 54 is illustrated as including the diffusion rate-controlling portion 54a, but the modification is not limited to the illustrated example.

Figure 10:
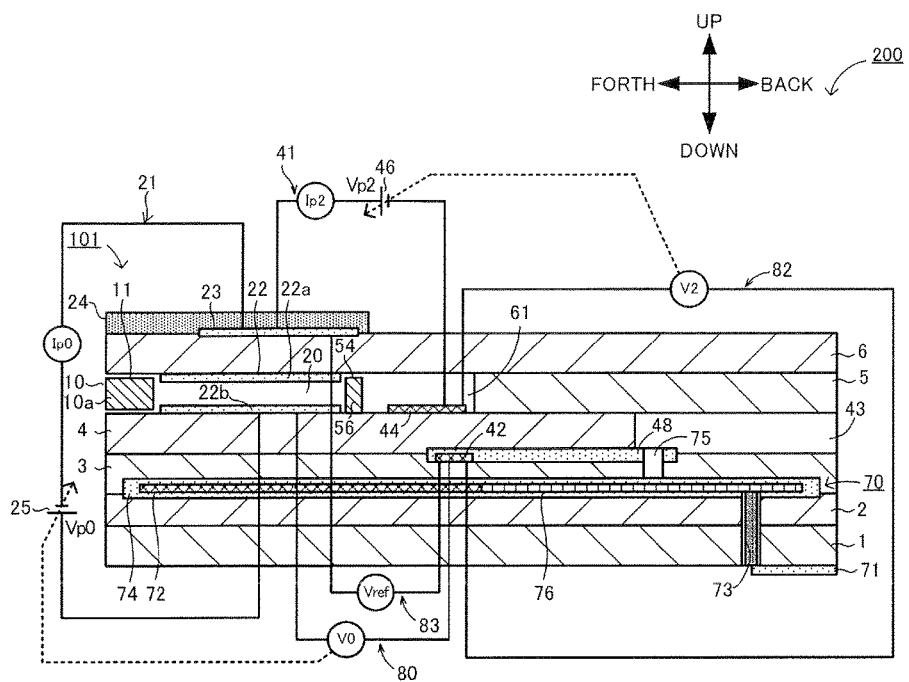
FIG. 10 is a schematic sectional view of a gas sensor 200 according to a modification.

While, in the above-described embodiment, the sensor element 101 of the gas sensor 100 includes the first inner cavity 20, the second inner cavity 40, and the third inner cavity 61, the present invention is not limited to that embodiment. For example, the sensor element 101 may have a structure not including the second inner cavity 40. FIG. 10 is a schematic sectional view of a gas sensor 200 according to a modification that represents the above-mentioned case. As illustrated in FIG. 10, in the gas sensor 200 according to this modification, the gas inlet 10, the first diffusion rate-controlling portion 11, the first inner cavity 20, the fourth diffusion rate-controlling portion 54, and the third inner cavity 61 are successively formed adjacent to each other in the mentioned order in a thoroughly communicating state between the lower surface of the second solid electrolyte layer 6 and the upper surface of the first solid electrolyte layer 4. Furthermore, unlike the above-described embodiment, the gas sensor 200 does not include the auxiliary pump cell 50, the oxygen partial-pressure detection sensor cell 81 for controlling the auxiliary pump. In the gas sensor 200 constituted as described above, the measurement object gas having the oxygen partial pressure, which is always held at a low constant value (i.e., a value substantially not affecting the measurement of NOx), is applied to the measurement pump cell 41 by operating the main pump cell 21. Thus, the concentration of NOx in the measurement object gas can be determined on the basis of the pump current Ip2 that flows upon pumping-out of oxygen by the measurement pump cell 41, the oxygen being generated with reduction of NOx substantially in proportion to the concentration of NOx in the measurement object gas. The gas sensor 200 constituted as described above can also suppress the reduction in sensitivity of the measurement electrode 44 by setting the positional relation between the fourth diffusion rate-controlling portion 54 and the measurement electrode 44 as in the above-described embodiment.

While, in the above-described embodiment, the sensor element 101 detects the concentration of NOx in the measurement object gas, the present invention is not limited to that embodiment insofar as the sensor element 101 detects the concentration of specific gas in the measurement object gas. For example, the sensor element 101 may detect the concentration of oxygen in the measurement object gas.

While the above-described embodiment represents an example in which the sensor element of the present invention is practiced as the sensor element 101 including the variable power supplies 25, 46 and 52, etc., the sensor element of the present invention may be practiced in the form of the sensor element 101 alone excluding the variable power supplies 25, 46 and 52, the external wirings, etc.

Moreover, since the measurement electrode 44 is formed on one of the upper, lower, left and right inner peripheral surfaces of the third inner cavity 61, the one surface being different in orientation from the surface along which the fourth diffusion rate-controlling portion 54 (the diffusion rate-controlling portion 54a) is formed, an effect of reducing an offset current (i.e., the pump current Ip2 generated when the specific gas (NOx) is not contained in the measurement object gas) can also be obtained. The reason is presumably as follows. In the related-art gas sensor 300 illustrated in FIG. 4, as described above, the portion of the measurement electrode 344 closer to its front end (e.g., the portion surrounded by the dotted line in FIG. 4) tends to be exposed to the measurement object gas having higher concentration with higher possibility. In other words, a concentration distribution of the measurement object gas in the surface of the measurement electrode 344 is more likely to become uneven. As a result, a current density in the measurement electrode 344 tends to cause a distribution (unevenness). Moreover, as described above, the pump current Ip2 is a current flowing when the voltage Vp2 of the variable power supply 46 is controlled such that the control voltage V2 (i.e., the electromotive force generated between the measurement electrode 44 and the reference electrode 42) is held constant. It is thought that, when the current density in the measurement electrode 344 tends to cause the unevenness, the pump current Ip2 used to hold the control voltage V2 constant tends to increase, and the offset current also tends to increase. In contrast, in this embodiment, since the measurement object gas having passed through the diffusion rate-controlling portion 54a reaches the measurement electrode 44 after having diffused in the third inner cavity 61, the concentration distribution of the measurement object gas in the surface of the measurement electrode 44 is less likely to become uneven in the surface of the measurement electrode 44. It is hence thought that the current density in the measurement electrode 44 is less apt to cause unevenness, and that the offset current is reduced consequently. In the case of meeting the condition that the distance L between the measurement electrode 44 and the fourth diffusion rate-controlling portion 54 is 0.1 mm or more, regardless of the measurement electrode 44 being formed at what position inside the third inner cavity 61, the concentration distribution of the measurement object gas is less likely to become uneven in the surface of the measurement electrode 44 and the effect of reducing the offset current is obtained as in the above-described case.

Figure 11:
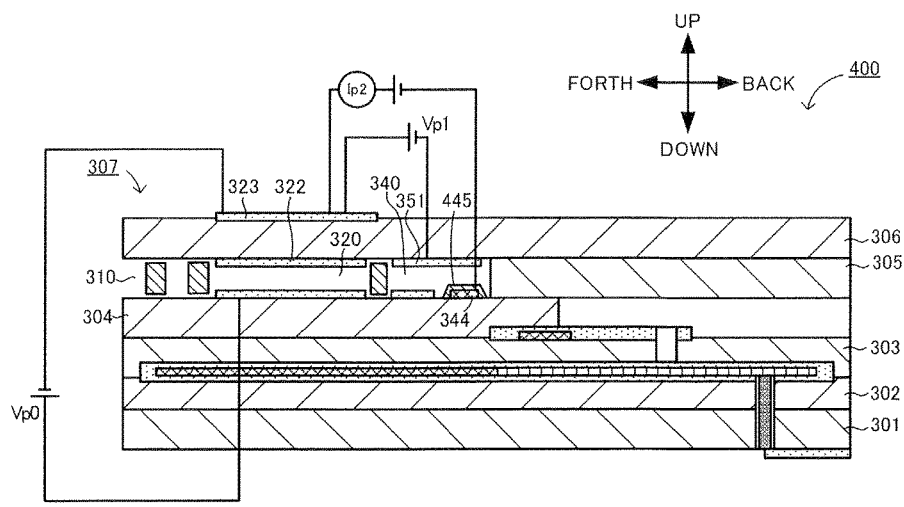
FIG. 11 is a schematic sectional view of a related-art gas sensor 400.

Additionally, there is so far known another related-art sensor element, such as a sensor element 400 illustrated in FIG. 11, which includes, instead of the fourth diffusion rate-controlling portion 54, an electrode protective layer 445 covering the measurement electrode 44 and made of a porous body, and which employs the electrode protective layer 445 as the diffusion rate-controlling portion. In the gas sensor constituted as described above, however, the electrode protective layer may be clogged with harmful components (e.g., Mg, Na and Ca) contained in the exhaust gas. With the clogging of the electrode protective layer, the measurement object gas may become harder to reach the measurement electrode and measurement accuracy may degrade in some cases. On the other hand, in the above-described embodiment, since the measurement electrode 44 is not covered with the electrode protective layer made of the porous body, the problem of clogging does not occur, and the reduction of measurement accuracy can be suppressed. Also in the case where the measurement electrode 44 is not covered with the electrode protective layer and the distance L between the measurement electrode 44 and the fourth diffusion rate-controlling portion 54 is 0.1 mm or more, the problem of clogging does not occur, and the reduction of measurement accuracy can be suppressed as in the above-described case. From the viewpoint of further suppressing the influence caused when harmful components in the measurement object gas adhere to the measurement electrode 44, the measurement electrode 44 is preferably made of a porous body having an average pore size of 3 μm or more.

Figure 12:
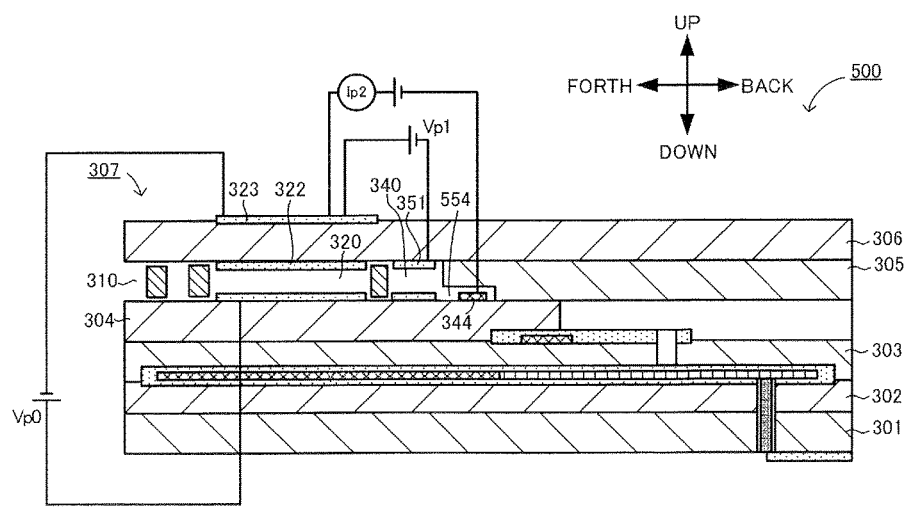
FIG. 12 is a schematic sectional view of a related-art gas sensor 500.

There is further known a sensor element 500 illustrated in FIG. 12, which aims to suppress the clogging of the above-mentioned electrode protective layer (see, e.g., PTL 2). In the sensor element 500, instead of forming the third inner cavity 361 and the slit-like diffusion rate-controlling portion 354 in the gas sensor 300 of FIG. 15, a diffusion rate-controlling portion 554 is formed rearward of the second inner cavity 340, and the measurement electrode 344 is exposed to a space of the diffusion rate-controlling portion 554. In the sensor element 400, the problem of clogging of the electrode protective layer does not occur. However, the portion of the measurement electrode 344 closer to its front end tends to be exposed to the measurement object gas having higher concentration with higher possibility as in the case of FIG. 4, and sensitivity of the measurement electrode 344 tends to reduce. In contrast, in the above-described embodiment, the problem of clogging of the electrode protective layer does not occur, and the reduction of sensitivity of the measurement electrode 44 can be suppressed.

EXAMPLES

The cases of practically fabricating the sensor elements will be described below as Examples. It is to be noted that the present invention is not limited to the following Examples.

Example 1

The sensor element 101, illustrated in FIGS. 1 to 3, was fabricated as Example 1 in accordance with the above-described manufacturing method. In fabricating the sensor element 101, the ceramic green sheets were each formed by mixing zirconia particles added with 4 mol % of yttria as a stabilizer, an organic binder, and an organic solvent, and by carrying out a tape forming process. The diffusion rate-controlling portion 54a in Example 1 had a height of 0.01 mm in the up and down direction, a width of 1.6 mm in the right and left direction, and a length of 0.6 mm in the back and forth direction. The third inner cavity 61 had a height of 0.1 mm in the up and down direction, a width of 1.2 mm in the right and left direction, and a length of 0.6 mm in the back and forth direction. The measurement electrode 44 had a thickness of 0.01 mm, a width of 1 mm in the right and left direction, and a length of 0.4 mm in the back and forth direction. The measurement electrode 44 was formed at such a position that the distance L was 0.14 mm.

Example 2

A sensor element was fabricated as Example 2 in the same manner as that in Example 1 except for setting the positional relation between the fourth diffusion rate-controlling portion 54 and the measurement electrode 44 to the relation illustrated in FIG. 9. Stated in another way, in Example 2, the fourth diffusion rate-controlling portion 54 included the diffusion rate-controlling portion 54a, and the measurement electrode 44 was formed on the rear surface 62f. The diffusion rate-controlling portion 54a had a height of 0.01 mm in the up and down direction, a width of 1.6 mm in the right and left direction, and a length of 0.6 mm in the back and forth direction. The measurement electrode 44 had a thickness of 0.01 mm, a length of 0.2 mm in the up and down direction, and a width of 1.6 mm in the right and left direction. The measurement electrode 44 was formed at such a position that the distance L was 0.6 mm.

Comparative Example 1

A sensor element was fabricated as Comparative Example 1 in the same manner as that in Example 1 except for setting the positional relation between the fourth diffusion rate-controlling portion 54 and the measurement electrode 44 to the relation illustrated in FIG. 4. Stated in another way, in Comparative Example 1, the fourth diffusion rate-controlling portion 54 included the diffusion rate-controlling portions 54a and 54b, and the measurement electrode 44 was formed on the lower surface 62b. Each of the diffusion rate-controlling portions 54a and 54b had the same shape as that in Example 2, and the measurement electrode 44 had the same shape as that in Example 1. The measurement electrode 44 was formed at such a position that the distance L was 0.02 mm.

Evaluation Tests

Figure 13:
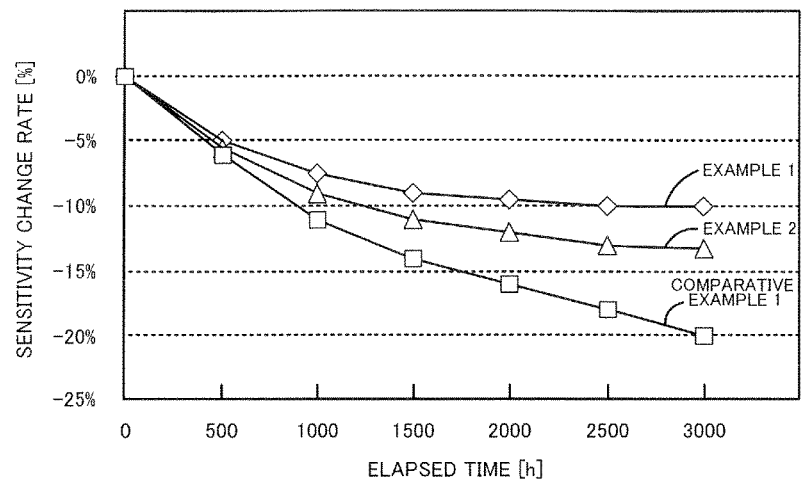
FIG. 13 is a graph representing relation between a sensitivity change rate and elapsed time in Examples 1 to 2 and Comparative Example 1.

Durability performance of the sensor elements of Examples 1 and 2 and Comparative Example 1 was evaluated by carrying out durability tests using a diesel engine. To simulate various operation modes and various exhaust gas components, the diesel engine was driven in pattern operations in which an engine rotation speed and a load were changed, and each sensor element was operated in exhaust gas. In such a state, the operation of the sensor element was continued for a predetermined lapsed time. The pattern operations were carried out at the engine rotation speed ranging from 1000 rpm to 3300 rpm and the load torque ranging from 0 to 350 Nm. The exhaust gas had a gas temperature of 200° C. to 600° C., oxygen concentration of 3% to 21%, and NOx concentration of 0 to 1500 ppm. After the lapse of the predetermined time, a value of a signal (i.e., the pump current Ip2 of the measurement pump cell 41), which was used to measure the NOx concentration in the sensor element, was measured in an atmosphere in which the NOx concentration was 500 ppm (nitrogen concentration=96.95%, oxygen concentration=0%, NOx concentration=500 ppm, and moisture=3%). The measurement of such a value of the signal was continued for each period of the predetermined lapsed time that was changed from 0 hour to 500 hours, 1000 hours, 1500 hours, 2000 hours, 2500 hours, and then to 3000 hours. The measurement results are plotted in FIG. 13. In FIG. 13, the value of the signal in each of Examples 1 and 2 and Comparative Example 1 when the lapsed time is 0 hour is assumed to be a reference value, and a plotted curve represents relation between a sensitivity change rate (signal change rate) from the reference value and the lapsed time. The graph means that, as an absolute value of the sensitivity change rate has a larger negative value, reduction of sensitivity in detection of the NOx concentration (i.e., reduction of sensitivity of the measurement electrode) with the lapse of time is larger (namely, the durability performance is lower). As seen from FIG. 13, any of Examples 1 and 2 had a tendency that, in comparison with Comparative Example 1, the sensitivity change rate did not so change with an increase of the lapsed time, and the absolute value of the sensitivity change rate was smaller (namely, the sensitivity change rate was closer to 0%). Thus, in Examples 1 and 2, the reduction of sensitivity of the measurement electrode 44 was suppressed in larger extent than in Comparative Example 1. Moreover, in Example 1, the reduction of sensitivity of the measurement electrode 44 was suppressed to a larger extent than in Example 2.

Comparison of Offset Currents

For each of the sensor elements of Example 1 and Comparative Example 1, the pump current Ip2 (i.e., the offset current) generated when the sensor element was operated in nitrogen gas not containing NOx was measured in the state before carrying out the above-described durability tests. The nitrogen gas had a gas temperature of 200° C., a gas flow rate of 200 L/min, oxygen concentration=0%, and NOx concentration=0 ppm, and moisture=3%. In Example 1, the offset current was lower than in Comparative Example 1 by 12%. Thus, in Example 1, the offset current was reduced to a larger extent than in Comparative Example 1.

Comparative Example 2

A sensor element was fabricated as Comparative Example 2 in the same manner as that in Example 1 except for including, instead of the fourth diffusion rate-controlling portion 54, the electrode protective layer 445 made of a porous body and covering the measurement electrode 44 as in the sensor element 400 illustrated in FIG. 11. The electrode protective layer 445 was fabricated by forming a pattern of alumina paste with the screen printing method using a metal mask, and by drying and firing the formed paste pattern. The electrode protective layer 445 had a thickness of 24 to 31 μm.

Comparison of Poisoning Resistance

Figure 14:
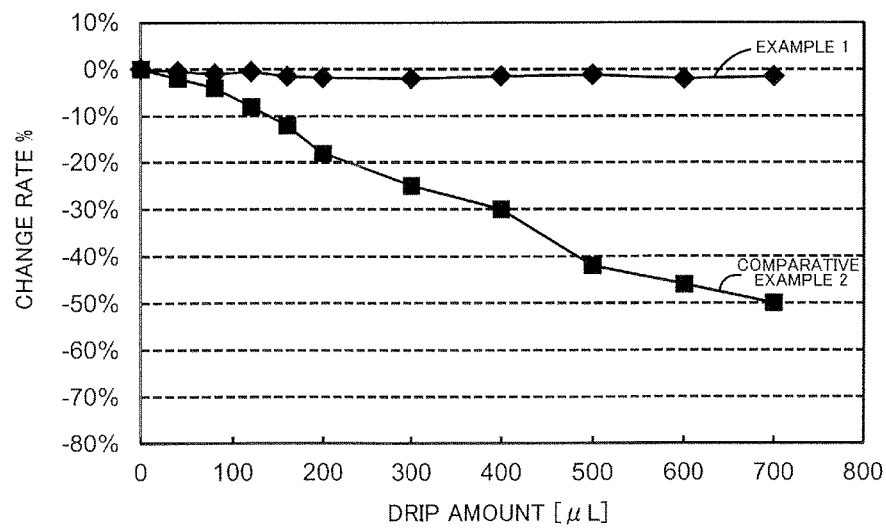
FIG. 14 is a graph representing relation between a drip amount of aqueous solution and a change rate in Example 1 and Comparative Example 2.

Poisoning resistance was compared between the sensor elements of Example 1 and Comparative Example 2. In more detail, the steps of dripping an aqueous solution containing ions of Mg, for example, onto a tip of each sensor element and operating the sensor element were repeated, and a change rate of the value of a signal (i.e., the pump current Ip2 of the measurement pump cell 41) with respect to an amount of the dripped aqueous solution was measured. The change rate was derived as a change rate of the value obtained when the aqueous solution was dripped, with respect to the value obtained when the aqueous solution was not dripped. The measured results are plotted in FIG. 14. As seen from FIG. 14, in Example 1, the value of the pump current Ip2 was hardly changed even after the aqueous solution was dripped until reaching 700 μL. On the other hand, in Comparative Example 2, the value of the pump current Ip2 was gradually reduced as the amount of the dripped aqueous solution was increased. From the above results, it was confirmed that, in Example 1, the poisoning resistance against harmful components, such as Mg, was higher and the reduction of measurement accuracy was kept smaller than those in Comparative Example 2.

The present application claims priority from Japanese Patent Application No. 2014-072927 filed on Mar. 31, 2014, and Japanese Patent Application No. 2015-063961 filed on Mar. 26, 2015, the entire contents of which are incorporated herein by reference.

What is claimed is:

1. A sensor element comprising:
a layered body that is formed by stacking a plurality of oxygen ion-conductive solid electrolyte layers, and that includes a measurement-object gas flowing portion formed therein to introduce measurement object gas from outside,
a measurement electrode mounting space that is a part of the measurement-object gas flowing portion, and that is partitioned from an inflow side of the measurement object gas by a partition wall,
at least one diffusion rate-controlling portion that is a part of the measurement-object gas flowing portion, that is formed, assuming a direction in which the solid electrolyte layers are stacked to be an up and down direction and a direction perpendicular to both the up and down direction and a direction in which the measurement object gas flows to be a right and left direction, between one or two surfaces of left and right inner peripheral surfaces of the measurement-object gas flowing portion and the partition wall, and that serves as a flow path through which the measurement object gas is introduced to the measurement electrode mounting space,
a measurement electrode that satisfies at least one of (a) and b,
(a) the measurement electrode is formed on one of upper, lower, left and right inner peripheral surfaces of the measurement electrode mounting space, the one surface being different in direction from the surface along which the diffusion rate-controlling portion is formed, and (b) the measurement electrode is formed in the measurement electrode mooting space at a position where a distance L between the measurement electrode and an exit of the diffusion rate-controlling portion is 0.1 mm or more.

2. The sensor element according to claim 1, wherein the diffusion rate-controlling portion is formed between one of the left and right inner peripheral surfaces of the measurement-object gas flowing portion and the partition wall, and;
the measurement electrode is formed on one of the left and right inner peripheral surfaces of the measurement electrode mounting space, the one surface being positioned on the side opposite to the surface along which the diffusion rate-controlling portion is formed.

3. The sensor element according to claim 1, wherein the measurement electrode satisfies (b), and is formed on one of inner peripheral surfaces of the measurement electrode mounting space, the one surface being perpendicularly to a direction in which the measurement object gas flows and being positioned on the downstream side in the flowing direction.

4. A gas sensor comprising the sensor element according to claim 1.

5. The sensor element according to claim 1, wherein the measurement electrode satisfies (b), and the distance L is 2.0 mm or less.

6. The sensor element according to claim 1, wherein the diffusion rate-controlling portion is open from an entrance to the exit thereof.

7. A sensor element comprising:
a layered body that is formed by stacking a plurality of oxygen ion-conductive solid electrolyte layers, and that includes a measurement-object gas flowing portion formed therein to introduce measurement object gas from outside, the flowing direction of the measurement-object gas flowing portion being perpendicular to the stacking direction of the layered body,
a measurement electrode mounting space that is a part of the measurement-object gas flowing portion,
at least one diffusion rate-controlling portion that is a part of the measurement-object gas flowing portion, that serves as a flow path through which the measurement object gas is introduced to the measurement electrode mounting space from the outside; and
a measurement electrode that is formed in the measurement electrode mounting space at a position where a distance L between the measurement electrode and an exit of the diffusion rate-controlling portion is in a range of 0.1 mm or more, and that is formed on one of inner peripheral surfaces of the measurement electrode mounting space, the one surface being arranged perpendicularly to a direction in which the measurement object gas flows and being positioned on the downstream side in the flowing direction.

8. A gas sensor comprising the sensor element according to claim 7.

9. The sensor element according to claim 7, wherein the distance L is 2.0 mm or less.

10. The sensor element according to claim 7, wherein the diffusion rate-controlling portion is open from an entrance to an exit thereof.

* * * * *